(12) United States Patent
Jackson et al.

(10) Patent No.: US 11,633,188 B2
(45) Date of Patent: Apr. 25, 2023

(54) DEVICE AND METHOD OF CREATING A FLUID CONTAINMENT FIELD FOR ADMINISTERING THERAPEUTICS TO A NERVE

(71) Applicant: Neuraptive Therapeutics, Inc., Winter Park, CO (US)

(72) Inventors: David M. Jackson, Winter Park, CO (US); Richard Trevino, York, PA (US); Jordan A. Hoffman, Broomfield, CO (US)

(73) Assignee: NEURAPTIVE THERAPEUTICS, INC., Chesterbrook, PA (US)

( * ) Notice: Subject to any disclaimer, the term of this patent is extended or adjusted under 35 U.S.C. 154(b) by 397 days.

(21) Appl. No.: 16/634,062

(22) PCT Filed: Jul. 24, 2018

(86) PCT No.: PCT/US2018/043549
§ 371 (c)(1),
(2) Date: Jan. 24, 2020

(87) PCT Pub. No.: WO2019/023274
PCT Pub. Date: Jan. 31, 2019

(65) Prior Publication Data
US 2021/0121181 A1    Apr. 29, 2021

Related U.S. Application Data

(60) Provisional application No. 62/537,388, filed on Jul. 26, 2017.

(51) Int. Cl.
*A61B 17/11* (2006.01)
*A61L 24/02* (2006.01)
(Continued)

(52) U.S. Cl.
CPC .......... *A61B 17/1128* (2013.01); *A61L 24/02* (2013.01); *A61L 24/046* (2013.01);
(Continued)

(58) Field of Classification Search
CPC ...... A61B 17/1128; A61B 2017/00893; A61B 2017/1132; A61B 90/04; A61M 31/002
See application file for complete search history.

(56) References Cited

U.S. PATENT DOCUMENTS 3,628,524 A    12/1971   Jamshidi
4,306,561 A *  12/1981   de Medinaceli ... A61B 17/1128
                                                      606/41

(Continued)

FOREIGN PATENT DOCUMENTS

RU    2585421     5/2016
SU    121532      11/1958
(Continued)

OTHER PUBLICATIONS

Bittner, G.D., et al. "Rapid, effective, and long-lasting behavioral recovery produced by microsutures, methylene blue, and polyethylene glycol after completely cutting rat sciatic nerves." Journal of neuroscience research 90.5 (2012) 967-980.
(Continued)

*Primary Examiner* — Mohamed G Gabr
(74) *Attorney, Agent, or Firm* — Knobbe Martens Olson & Bear LLP

(57) ABSTRACT

A severed nerve may be surgically rejoined and severed axons fused via sequential administrations of solutions. The solutions may include a priming solution comprising methylene blue in a $Ca^{2+}$-free saline solution, a fusion solution comprising about 50% (w/w) PEG, and a sealing solution comprising $Ca^{2+}$-containing saline. The PEG fusion solution may be applied in a nerve treatment device configured to
(Continued)

isolate the injured segment of the nerve. The device may include a containment chamber for creating a fluid containment field around the anastomosis. The device may have slits, slots, and/or apertures in opposing endwalls of the device designed to receive the nerve. The device may have an open bath configuration or may include separable lower and upper bodies to create a closed bath configuration. The device may include one or more fluid ports in fluid communication with the containment chamber for introducing and/or removing fluid.

17 Claims, 19 Drawing Sheets

(51) Int. Cl.
  *A61L 24/04* (2006.01)
  *A61M 31/00* (2006.01)
  *A61B 17/00* (2006.01)
(52) U.S. Cl.
  CPC .. *A61M 31/002* (2013.01); *A61B 2017/00893* (2013.01); *A61B 2017/1132* (2013.01); *A61L 2300/802* (2013.01)

(56) References Cited

U.S. PATENT DOCUMENTS

| | | | |
|---|---|---|---|
| 4,573,471 A * | 3/1986 | Rudner | A61B 17/11 600/561 |
| 4,662,884 A | 5/1987 | Stensaas et al. | |
| 4,778,467 A * | 10/1988 | Stensaas | A61F 2/04 606/152 |
| 5,972,371 A | 10/1999 | Gilchrist et al. | |
| 6,102,921 A | 8/2000 | Zhu et al. | |
| 10,398,438 B2 | 9/2019 | Bittner | |
| 2002/0107527 A1 | 8/2002 | Burres | |
| 2003/0055414 A1 | 3/2003 | Altshuler et al. | |
| 2003/0118545 A1 | 6/2003 | Shi et al. | |
| 2004/0172045 A1 | 9/2004 | Eriksson et al. | |
| 2004/0186489 A1 | 9/2004 | Lee | |
| 2005/0028828 A1 | 2/2005 | Heaton et al. | |
| 2006/0259102 A1 | 11/2006 | Slatkine | |
| 2007/0250082 A1 | 10/2007 | Kansoul | |
| 2010/0168625 A1 | 7/2010 | Swain et al. | |
| 2010/0168831 A1 | 7/2010 | Korivi et al. | |
| 2010/0211172 A1 | 8/2010 | Bellamkonda et al. | |
| 2011/0257588 A1 | 10/2011 | Knowlton | |
| 2012/0035618 A1 | 2/2012 | Sabir et al. | |
| 2014/0107590 A1 | 4/2014 | Winograd | |
| 2014/0163586 A1 * | 6/2014 | Holt | A61B 17/083 606/151 |
| 2014/0163587 A1 * | 6/2014 | Yang | A61B 17/1128 606/152 |

FOREIGN PATENT DOCUMENTS

| | | |
|---|---|---|
| SU | 1438938 | 11/1988 |
| WO | WO 2012/133019 | 10/2012 |
| WO | WO 2012/161823 | 11/2012 |
| WO | WO 2017/079726 | 5/2017 |

OTHER PUBLICATIONS

Britt, Joshua M., et al. "Polyethylene glycol rapidly restores axonal integrity and improves the rate of motor behavior recovery after sciatic nerve crush injury," Journal of neurophysiology 104.2 (2010): 695-703.
International Preliminary Report on Patentability issued in International Application No. PCT/US2012/026764, dated Aug. 27, 2013.
International Search Report issued in International Application No. PCT/US2012/026767, dated Apr. 26, 2012.
International Written Opinion issued in International Application No. PCT/US2012/026764, dated Apr. 26, 2012.
Krause, Todd L., and George D. Bittner. "Rapid morphological fusion of severed myelinated axons by polyethylene glycol." Proceedings of the National Academy of Sciences 87.4 (1990): 1471-1475.
Lore, April B., et al. "Rapid induction of functional and morphological continuity between severed ends of mammalian or earthworm myelinated axons." Journal of Neuroscience 19.7 (1999): 2442-2454.
Stavisky, Ronda C., et al. "Melatonin enhances the in vitro and in vivo repair of severed rat sciatic axons." Neuroscience letters 376.2 (2005): 98-101.
U.S. Appl. No. 17/789,640, filed Dec. 31, 2013 with the United States Patent and Trademark Office.
Marzullo, et al., "Cooling enhances in vitro survival and fusion-repair of severed axons taken from the peripheral and central nervous systems of rats." Neuroscience Letters 327 (2002) 9-12.
Spaeth, et al., "Cellular Mechanisms of Plasmalemmal Sealing and Axonal Repair by Plyethylene Glycol and Methylene Blue." Journal of Neuroscience Research 90:955-966 (2012).
Krause, Todd L., "Rapid artificial restoration of electrical continuity across a crush lesion of a giant axon." Brain Researc, 561 (1991) 350-353.
Bittner, George D., "Reconnection of severed nerve axons with polyethylene glycol." Brain Research, 367(1986) 351-355.

\* cited by examiner

DEVICE AND METHOD OF CREATING A FLUID CONTAINMENT FIELD FOR ADMINISTERING THERAPEUTICS TO A NERVE

BACKGROUND

Description of the Related Art

No known devices serve the functions of 1) creating an isolated fluid containment field for topical (on the nerve) delivery of pharmaceutical solutions to focal regions of a nerve; 2) protecting tissues other than the nerve to be treated from exposure to the pharmaceutical solutions; and 3) providing a design that can be placed and withdrawn from the nerve without damage to the anastomosis. None also provide for a method of using a delivery device in sequence for repairing a nerve using PEG-fusion.

The following patents and published applications may be of relevance to the field and are hereby incorporated by reference in their entirety: U.S. Pub. No.: 2005/0028828; U.S. Pub. No.: 2003/0055414; U.S. Pub. No.: 201/0035618; U.S. Pub. No.: 2004/0172045; U.S. Pub. No.: 2006/0259102; U.S. Pub. No.: 2011/0257588; U.S. Pub. No.: 2002/0107527; U.S. Pub. No.: 2014/0107590; and U.S. Pat. No. 3,628,524.

SUMMARY

Polyethylene glycol fusion (PEG-fusion) is an emerging technology for the acute repair of injured peripheral and central nerves. Injured peripheral nerve repair is made by suturing the cut ends back together, inserting bridging devices, and engrafting donated segments of nerve. None of the current repairs actually restores function and sensation but instead merely facilitates natural nerve regeneration. In contrast, PEG-fusion does immediately restore function and sensation as well as prevents degeneration, blocks distal target tissue atrophy, and results in dramatically faster and significantly improved recovery of sensation and function.

PEG-fusion consists of the sequential administration of a series of pharmaceutical agents that cause severed axons within a nerve bundle to fuse and reconstitute axonal integrity. Without being limited by theory, PEG-fusion uses PEG, which is highly hydrophilic, as a dehydrating agent causing removal of bound water from the extracellular surfaces of cellular plasma membranes and promoting the plasma membranes of exposed cells to fuse together. This is performed in the operating theater and is an addition to the standard of care-microsuturing of the proximal and distal ends through the epineurium (neurorrhaphy).

The concentration of PEG used during the PEG administration step in the method may be about 50% (w/w) and could pose an exposure risk to uninvolved nerve and tissues adjacent to the nerve being repaired. Exposure to high concentrations of PEG have been shown to 1) destroy a nerve's electrophysiological function; 2) and cause other soft tissues to become necrotic.

As such, the device contemplated herein may advantageously: 1) Provide for placement of the device such as to not disturb the recently sutured nerve; 2) Create a fluid containment field surrounding a sutured nerve; 3) Provide for a sustained and consistent exposure of the injured, sutured nerve segment; 4) Prevent unnecessary exposure of the uninjured segments of the nerve to PEG; 5) Prevent unnecessary exposure of the adjacent tissues to PEG; 6) Provide for convenient and efficient removal of the PEG after the administration step; and/or 7) Provide for a removal of the device such as to not disturb the recently fused axons within the recently fused nerve.

The delivery device disclosed herein may allow for qualitative and/or quantitative evaluation of the restoration of electrophysiological activity across a restored nerve by measuring compound action potentials (CAPs) across the anastomosis of nerves that had been severed, sutured and PEG-fused. Compound action potentials (CAPs) measure the cumulative electrical signal recorded extracellularly from a population of axons, such as within in a nerve. The device may also allow for the demonstration of the destruction of electrophysiological activity caused by excessive exposure (in time and/or concentration) of PEG by measuring compound action potentials (CAPs) across the anastomosis of nerves that had been severed, sutured and PEG-fused nerves. For example, nerves exposed to continuous 50% (w/w) PEG for 20 or more minutes may show deleterious effects. The design of the device may be configured to provide the least impact to the nerve during device placement, administration of PEG and device removal.

Other applications of the method of PEG-fusion with the delivery device may include repair of injured spinal column nerves; engraftment of segments of peripheral nerves into segments ablated by trauma including allografts, autografts and xenografts; and any other suitable application.

Disclosed herein is a nerve treatment device for forming a fluid containment field around at least at least a portion of an isolated segment of a nerve. The nerve treatment device includes an elongate body and a containment chamber formed within the elongate body. The elongate body extends from a first endwall to a second endwall substantially opposite the first endwall. The elongate body has a top surface and a longitudinal axis extending from the first endwall to the second endwall. The containment chamber extends from the first endwall to the second endwall and has a void volume intersecting the top surface to form an access area. The access area is configured to receive the isolated segment of the nerve into the containment chamber and the containment chamber is configured to substantially retain a volume of fluid within the void volume around at least a portion of the isolated segment of the nerve. The first endwall includes a first aperture opening into the containment chamber and the second endwall includes a second aperture opening into the containment chamber. The first and second apertures are configured to retain first and second ends of the isolated segment of the nerve, respectively, and to form fluid seals around the first and second ends of the isolated segment of the nerve, respectively. The first endwall includes a first slit extending through the first endwall from the top surface to the first aperture and the second endwall includes a second slit extending through the second endwall from the top surface to the second aperture. At least a portion of the first endwall is flexible and configured to be biased in a manner that increases a first width between opposing edges of the first slit so that the nerve may be received through the first slit into the first aperture. At least a portion of the second endwall is flexible and configured to be biased in a manner that increases a second width between opposing edges of the second slit so that the nerve may be received through the second slit into the second aperture.

The flexible portion of the first endwall may include a first flange having a thickness which tapers in a distal direction of the first flange. A distal edge of the first flange can be defined by the first slit. The flexible portion of the first endwall may include a second flange having a thickness which tapers in a distal direction of the second flange. A distal edge of the second flange can be defined by the first slit, such that the distal edges of the first and second flanges form opposing edges of the first slit. The first and second apertures may be positioned in the first and second endwalls such that the bottoms of the first and second apertures opposite the top surface are elevated above a floor of the containment chamber. The containment chamber may have beveled and/or curved surfaces interconnecting the bottoms of the first and second apertures to the floor of the containment chamber. The beveled and/or curved surfaces may be configured to help support the weight of the isolated segment of the nerve.

The containment chamber may be configured to retain the volume of fluid such that the fluid entirely surrounds a circumference of the nerve along at least a portion of the isolated segment of the nerve. The width of the access area may be greater than a width of the first aperture and greater than a width of the second aperture. The first and second apertures may be circular. The first and second apertures may have diameters in an unbiased configuration slightly smaller than a diameter of the nerve such that the first and second apertures are configured to form compressive seals around the nerve when received within the first and second apertures. The first and second apertures may be longitudinally aligned.

A bottom surface of the elongate body may be generally rounded. At least a portion of the bottom surface of the elongate body can be flattened so that the device may rest stably on a flat surface. The first endwall may have a profile shape corresponding to a portion of an obround. The depth of the containment chamber may increase between front and rear ends of the containment chamber. The front and rear ends may extend from the first endwall to the second endwall. A floor of the containment chamber may not be flat. The elongate body and the endwalls may be integrally fabricated from the same material. The elongate body may comprise silicone. The silicone may comprise medical grade polydimethyl siloxane (PDMS).

The nerve treatment device may include a handle extending laterally from the elongate body. The handle may extend from a rear side of the device between the first and second endwalls. The handle may have an elongate body. The handle may have a textured surface. The handle may have a top surface that is flush with the top surface of the elongate body. The handle may extend horizontally in a rearward direction. The handle may curve or angle in an upward direction and/or in a downward direction. The handle may have a proximal end joined to the elongate body and a distal end opposite the proximal end. The distal end may be positioned above or below the top surface of the elongate body. The handle may include a curvature having an inflection point.

The first slit may bisect the first aperture and the second slit may bisect the second aperture. The first aperture and the second aperture may be horizontally centered within the first and second endwalls, respectively, between front and rear ends of the elongate body.

The first aperture and the second aperture may horizontally disposed more towards the front end of the elongate body. The first slit may divide an inner front surface of the containment chamber from an inner surface of the first endwall and the second slit may divide the inner front surface of the containment chamber from an inner surface of the second endwall, such that a front wall of the elongate body formed between the first slit and the second slit is configured to be biased in a frontward direction in a manner that increases the first width and the second width. The first slit may intersect a front edge of the first aperture and the second slit may intersect a front edge of the second aperture. A front wall of the elongate body may have an angled edge on the top surface sloping downward toward the containment chamber.

The nerve treatment device may include an enclosed fluid channel formed within the elongate body. The fluid channel may have a first opening interfacing the containment chamber and a second opening on an external surface of the device not interfacing the containment chamber. Fluid may be introduced into and/or removed from the containment chamber via the fluid channel. The second opening may be formed on a fluid port extending from the elongate body. The fluid port may include a luer connector configured to couple to a syringe. The fluid port may extend from a distal end of a handle extending from the elongate body. The nerve treatment device may include a second enclosed fluid channel formed within the elongate body, the fluid channel having a third opening interfacing the containment chamber and a fourth opening on an external surface of the device not interfacing the containment chamber. Fluid may be introduced into and/or removed from the containment chamber via the second fluid channel.

In another aspect of the present disclosure, disclosed herein is a nerve treatment device for forming a fluid containment field around at least a portion of an isolated segment of a nerve. The nerve treatment device has an elongate body and a containment chamber formed within the elongate body. The elongate body extends from a first endwall to a second endwall substantially opposite the first endwall. The elongate body includes a lower body and an upper body and has a longitudinal axis extending from the first endwall to the second endwall. The containment chamber extends from the first endwall to the second endwall. The containment chamber is configured to substantially retain a volume of fluid in a void volume of the containment chamber around at least a portion of the isolated segment of the nerve. The first endwall includes a first aperture opening into the containment chamber and the second endwall includes a second aperture opening into the containment chamber. The first and second apertures are configured to retain first and second ends of the isolated segment of the nerve, respectively, and to form fluid seals around the first and second ends of the isolated segment of the nerve, respectively. The lower body and the upper body may be at least partially divided by a split extending the length of the elongate body. The split extends from a front side of the elongate body inward to the first and second apertures. The split defines a top surface of the lower body and a bottom surface of the lower body. A separation distance between the lower body and the upper body can be increased along the split such that the elongate body is configured to receive the nerve through the split and into the first and second apertures. The lower body and upper body are configured to substantially enclose an entire circumference of the nerve in a closed configuration.

The lower body and the upper body may be joined together at a rear side of the elongate body. The lower body and the upper body may be joined together by a flexible hinge. The flexible hinge may be a living hinge. The lower body and the upper body may be integral at the rear side of the elongate body. The elongate body may have a generally tubular body comprising a sidewall defining a circumference. The split may extend through the sidewall along the front side, the circumference being openable along the length of the split, and the sidewall being uninterrupted along the rear side. The split may not extend rearward of the first aperture or the second aperture. The upper body may be entirely separable from the lower body. The void volume of the containment chamber may be formed in the lower body and the upper body. The void volume of the containment chamber may be formed entirely in the lower body and the upper body may be configured to seal an access area formed in the top surface of the lower body which opens into the void volume.

The first endwall may be flat. At least a portion of the first endwall may have a frustoconical shape wherein the first aperture forms an apex of the frustoconical shape. The first endwall may include a sidewall having a thickness that decreases as the sidewall extends toward the apex of the frustoconical shape.

The lower body may include a first locking feature and the upper body may have a second locking feature configured to engage the first locking feature to lock the lower body and the upper body together in the closed configuration. The first and second locking features may include a ridge and a trench configured to mate together to form an interference fit. The nerve treatment device may include a lower lip and an upper lip, the split extending between the lower lip and the upper lip. The lower lip and the upper lip may be configured to receive a securing mechanism to maintain the lower body and the upper body in a closed configuration. The lower lip and/or the upper lip may include a groove extending along at least a partial length of the lip to retain the securing mechanism.

The elongate body may have a generally cylindrical shape. The containment chamber may include beveled and/or curved surfaces interconnecting the bottoms of the first and second apertures to the floor of the containment chamber. The beveled and/or curved surfaces may be configured to help support the weight of the isolated segment of the nerve. The containment chamber may be configured to retain the volume of fluid such that the fluid entirely surrounds a circumference of the nerve along at least a portion of the isolated segment of the nerve. The width of the access area may be greater than a width of the first aperture and greater than a width of the second aperture. The first and second apertures may be circular. The first and second apertures may have diameters in an unbiased configuration slightly smaller than a diameter of the nerve such that the first and second apertures are configured to form compressive seals around the nerve when received within the first and second apertures. The first and second apertures may be longitudinally aligned. The first aperture and the second aperture may be horizontally centered within the first and second endwalls, respectively, between front and rear ends of the elongate body.

At least a portion of the bottom surface of the elongate body can be flattened so that the device may rest stably on a flat surface. The depth of the containment chamber may increase between front and rear ends of the containment chamber, the front and rear ends extending from the first endwall to the second endwall. The floor of the containment chamber may not be flat. The elongate body and the endwalls may be integrally fabricated from the same material. The elongate body may comprise silicone. The silicone may comprise medical grade polydimethylsiloxane (PDMS).

The nerve treatment device may include a handle extending laterally from the elongate body. The handle may extend from a rear side of the device between the first and second endwalls. The handle may have an elongate body. The handle may have a textured surface. The handle may have a top surface that is flush with the top surface of the elongate body. The handle may extend horizontally in a rearward direction. The handle may curve or angle in an upward direction and/or in a downward direction. The handle may have a proximal end joined to the elongate body and a distal end opposite the proximal end. The distal end may be positioned above or below the top surface of the elongate body. The handle may include a curvature having an inflection point. The upper body may be indirectly coupled to the handle via a connecting arm. The connecting arm can be manipulated to move the lower body and upper body between the closed configuration and an opened configuration.

The nerve treatment device may include an enclosed fluid channel formed within the elongate body. The fluid channel may have a first opening interfacing the containment chamber and a second opening on an external surface of the device not interfacing the containment chamber. Fluid may be introduced into and/or removed from the containment chamber via the fluid channel. The second opening may be formed on a fluid port extending from the elongate body. The fluid port may include a luer connector configured to couple to a syringe. The fluid port may extend from a distal end of a handle extending from the elongate body. The nerve treatment device may include a second enclosed fluid channel formed within the elongate body, the fluid channel having a third opening interfacing the containment chamber and a fourth opening on an external surface of the device not interfacing the containment chamber. Fluid may be introduced into and/or removed from the containment chamber via the second fluid channel.

In another aspect of the present disclosure, disclosed herein is a nerve treatment device for forming a fluid containment field around at least at least a portion of an isolated segment of a nerve. The nerve treatment device has an elongate body and a containment chamber formed within the elongate body. The elongate body extends from a first endwall to a second endwall substantially opposite the first endwall. The elongate body has a top surface and a longitudinal axis extending from the first endwall to the second endwall. The containment chamber extends from the first endwall to the second endwall. The containment chamber has a void volume intersecting the top surface to form an access area. The access area is configured to receive the isolated segment of the nerve into the containment chamber. The containment chamber is configured to substantially retain a volume of fluid within the void volume around at least a portion of the isolated segment of the nerve. The first endwall includes a first slot extending downward from the top surface configured to receive and retain a first end of the isolated segment of the nerve and the second endwall includes a second slot extending downward from the top surface configured to receive and retain a second end of the isolated segment of the nerve. The first and second slots are configured to form fluid seals around at least bottom portions of the isolated segment of the nerve.

The first endwall may be formed by an edge of a sidewall forming a front side, rear side, and bottom side of the elongate body, such that no portion of the endwall forms an inner surface of the containment chamber. A width of the containment chamber transverse to the longitudinal axis may vary continuously across a length of the containment chamber. The containment chamber may have a maximum width between the first endwall and the second endwall. A depth of the containment chamber may vary continuously across a length of the containment chamber. The containment chamber may have a maximum depth between the first endwall and the second endwall. A depth of the containment chamber may vary continuously across a width of the containment chamber. The containment chamber may have a maximum depth between a front side and a rear side of the containment chamber. The floor of the containment chamber may not include a flat surface. A width of the elongate body transverse to the longitudinal axis may vary continuously across a length of the elongate body. The elongate body may have a maximum width between the first endwall and the second endwall.

In another aspect of the present disclosure, disclosed herein is a nerve treatment device for forming a fluid containment field around at least at least a portion of an isolated segment of a nerve. The nerve treatment device has an elongate body and a containment chamber formed within the elongate body. The elongate body extends from a first endwall to a second endwall substantially opposite the first endwall. The elongate body has a top surface and a longitudinal axis extending from the first endwall to the second endwall. The containment chamber extends from the first endwall to the second endwall. The containment chamber has a void volume intersecting the top surface to form an access area. The access area is configured to receive the isolated segment of the nerve into the containment chamber and the containment chamber is configured to substantially retain a volume of fluid within the void volume around at least a portion of the isolated segment of the nerve. The first endwall includes a first slit extending through the first endwall from the top surface downward and the second endwall includes a second slit extending through the second endwall from the top surface downward. At least a portion of the first endwall is flexible and configured to be biased in a manner that increases a first width between opposing edges of the first slit so that the nerve may be received through the first slit. At least a portion of the second endwall is flexible and configured to be biased in a manner that increases a second width between opposing edges of the second slit so that the nerve may be received through the second slit.

The first slit may extend to the bottom of the portion of the containment chamber adjacent to the first endwall. The first slit may bisect the first endwall. The flexible portion of the first endwall may include a first flange having a thickness which tapers in a distal direction of the first flange. A distal edge of the first flange can be defined by the first slit. The flexible portion of the first endwall may include a second flange having a thickness which tapers in a distal direction of the second flange. A distal edge of the second flange can be defined by the first slit, such that the distal edges of the first and second flanges form opposing edges of the first slit. The first slit may extend along at least a portion of the intersection between the first endwall and the bottom portion of the containment chamber adjacent to the first endwall.

In another aspect of the present disclosure, disclosed herein is a nerve treatment device for forming a fluid containment field around at least at least a portion of an isolated segment of a nerve. The nerve treatment device has an elongate body extending from a first endwall to a second endwall substantially opposite the first endwall. The elongate body has a lower body and an upper body and a longitudinal axis extending from the first endwall to the second endwall. The nerve treatment device includes a containment chamber formed within the lower body and extending from the first endwall to the second endwall. The containment chamber has a void volume intersecting a top surface of the lower body to form an access area. The access area is configured to receive the isolated segment of the nerve into the containment chamber and the containment chamber is configured to substantially retain a volume of fluid within the void volume around at least a portion of the isolated segment of the nerve. The first endwall includes a first aperture opening into the containment chamber and the second endwall includes a second aperture opening into the containment chamber. The first and second apertures are configured to retain first and second ends of the isolated segment of the nerve, respectively, and to form fluid seals around bottom portions of the first and second ends, respectively. The upper body is configured to be received within the containment chamber to form a fluid seal with an upper portion of the containment chamber such that the entire access area of the top surface is occluded. The lower body and upper body are configured to substantially enclose an entire circumference of the nerve in a closed configuration.

The lower body may be joined to the upper body when the device is in an open configuration in which the containment chamber is not sealed. The lower body may be joined to the upper body by a hinge. The hinge may be a living hinge. The upper body may include a first downward extension configured to be received in the first aperture over the first end of the nerve. The first extension may be configured to seal the first aperture around a top portion of the first end of the nerve. The first extension may form an inner lateral surface of the containment chamber. The first extension may have a concave bottom edge configured to conform to the shape of the nerve.

The containment chamber may include a plurality of support ribs extending vertically along the depth of the containment chamber. Two support ribs may be positioned opposite each other on front and rear inner surfaces of the containment chamber. The support ribs may be spaced so as to support the isolated segment of the nerve over a floor of the containment chamber.

In another aspect of the present disclosure, disclosed herein is a delivery device for performing a nerve repair procedure. The delivery device has an elongate body extending from a first end to a second end and a longitudinal axis. The delivery device includes a containment chamber within the elongate body for receiving a rejoined nerve. The containment chamber has a first opening at the first end of the elongate body, a second opening at the second end of the elongate body, and an elongate opening extending parallel to the longitudinal axis from the first opening to the second opening for introducing the rejoined nerve into the containment chamber. The delivery device includes a port in fluid communication with the containment chamber and configured to couple with a syringe for the injection of solutions into the containment chamber. The delivery device includes a handle extending from the elongate body configured for facilitating placement of the delivery device around a nerve.

In another aspect of the present disclosure, disclosed herein is a method of repairing a severed nerve. The method includes physically rejoining the severed nerve such that axon-to-axon contact is restored; placing a delivery device around the rejoined nerve; and inducing fusion of severed axons within the rejoined nerve by introducing a fusion solution into a containment chamber of the delivery device and incubating the rejoined nerve in the fusion solution. The delivery device has an elongate body and the containment chamber is formed within the elongate body. The elongate body extends from a first end to a second end of the delivery device and has a longitudinal axis. The containment chamber is configured for receiving the rejoined nerve. The containment chamber has a first opening at the first end of the elongate body, a second opening at the second end of the elongate body, and an elongate opening extending parallel to the longitudinal axis from the first opening to the second opening for introducing the rejoined nerve into the containment chamber. Placing the delivery device around the rejoined nerve includes introducing the rejoined nerve through the longitudinal opening into the containment chamber.

The method may include irrigating or incubating the ends of severed axons in a priming solution comprising $Ca^{2+}$-free saline prior to physically rejoining the severed nerve. The priming solution may comprise methylene blue, which, in some embodiments, may be at approximately 1% (w/V). The method may include sealing any remaining membrane discontinuity of the fused axonal membranes by rinsing or incubating the rejoined nerve with a sealing solution comprising $Ca^{2+}$-containing saline. The rinsing or incubating of the rejoined nerve with the sealing solution may be performed within the containment chamber and/or outside the containment chamber. The sealing solution may comprise calcium chloride ($CaCl_2$), which in some embodiments, may be at approximately 0.02% (w/V).

Physically rejoining the severed nerve may include suturing a proximal end and a distal end of the severed nerve together. The physically rejoining the severed nerve may be performed in the presence of the priming solution.

The method may include removing the fusion solution from the containment chamber by aspiration. The method may include removing the delivery device from around the nerve. The fusion solution may comprises low molecular weight polyethylene glycol (PEG). The concentration of PEG may be no greater than approximately 50% (w/w). The concentration of PEG may be approximately 50% (w/w). The PEG may be low molecular weight PEG having an average molecular weight no greater than 5,000 Da or 3,500 Da. The PEG may have an average molecular weight of approximately 3,350 Da.

The method may include irrigating or incubating the anastomosis of the rejoined nerve in the priming solution prior to fusing the axons. The irrigating or incubating of the rejoined nerve in priming solution may be performed after placing the delivery device around the rejoined nerve.

The delivery device may include a port in fluid communication with the containment chamber. Introducing the fusion solution may comprise introducing the fusion through the port into the containment chamber. The port may be configured to couple with a syringe for the injection of solutions into the containment chamber.

The nerve may be exposed to the fusion solution for no longer than 2 minutes. The nerve may be exposed to the priming solution for no longer than 2 minutes. The nerve may be exposed to the sealing solution for no longer than 2 minutes.

In another aspect of the present disclosure, disclosed herein is a method of repairing a severed nerve. The method includes irrigating the ends of severed axons in a priming solution comprising 1% (w/V) methylene blue in hypotonic $Ca^{2+}$-free saline and physically rejoining the severed nerve by suturing a proximal end and a distal end of the severed nerve together in the presence of the priming solution such that axon-to-axon contact is restored. The method further includes placing a delivery device around the rejoined nerve. The delivery device has an elongate body extending from a first end to a second end and a longitudinal axis. The delivery device has a containment chamber within the elongate body for receiving the rejoined nerve. The containment chamber has a first opening at the first end of the elongate body, a second opening at the second end of the elongate body, and an elongate opening extending parallel to the longitudinal axis from the first opening to the second opening for introducing the rejoined nerve into the containment chamber. Placing the delivery device around the rejoined nerve comprises introducing the rejoined nerve through the longitudinal opening into the containment chamber. The method further includes inducing fusion of severed axons within the rejoined nerve by introducing a fusion solution into the containment chamber and incubating the rejoined nerve in the fusion solution. The fusion solution comprises about 50% (w/w) low molecular weight PEG. The method further includes removing the fusion solution from the containment chamber by aspiration and removing the delivery device from around the nerve. The method further includes sealing any remaining membrane discontinuity of the fused axonal membranes by rinsing the rejoined nerve with a saline sealing solution comprising isotonic $Ca^{2+}$-containing saline.

In another aspect of the present disclosure, disclosed herein is a kit including a nerve treatment device and one or more of the solutions from any one of the solutions described above.

BRIEF DESCRIPTION OF THE DRAWINGS

FIG. 3A depicts a right cross-sectional view of the treatment device. FIG. 3B depicts a left cross-sectional view of the treatment device. FIG. 3C depicts a rear view of the treatment device. FIG. 3D depicts a front view of the treatment device. FIG. 3E depicts a perspective view of the treatment device.

FIG. 4A depicts a perspective view of the treatment device. FIG. 4B depicts a front view of the treatment device. FIG. 4C depicts a cross-sectional view of section A-A indicated FIG. 4B. FIG. 4D depicts a view of the left side of the treatment device.

FIG. 5A depicts a perspective view of the treatment device. FIG. 5B depicts a top view of the treatment device. FIG. 5C depicts a left side view of the treatment device.

FIG. 6A depicts a perspective view of the treatment device. FIG. 6B depicts a top view of the treatment device. FIG. 6C depicts a front view of the treatment device. FIG. 6D depicts a cross-sectional view of the section B-B indicated in FIG. 6C. FIG. 6E depicts a right side view of the treatment device. FIG. 6F depicts a close-up view of the inset A indicated in FIG. 6E. FIG. 6G depicts a perspective view of a variation of the treatment device illustrated in FIG. 6A.

FIG. 8A depicts a perspective view of the treatment device 800. FIG. 8B depicts a top view of the treatment device. FIG. 8C depicts a left or right side view of the treatment device. FIG. 8D depicts a front or rear view of the treatment device. FIG. 8E depicts a cross-sectional view of the section A-A indicated in FIG. 8D.

FIG. 11A depicts a perspective view of the treatment device. FIG. 11B depicts a top view of the treatment device. FIG. 11C depicts a right side view of the treatment device. FIG. 11D depicts a rear view looking down on a portion of the handle of the treatment device. FIG. 11E depicts a cross-sectional view of a section taken along a midline between left and right sides of the treatment device transverse to the longitudinal axis.

DETAILED DESCRIPTION

Figure 1:
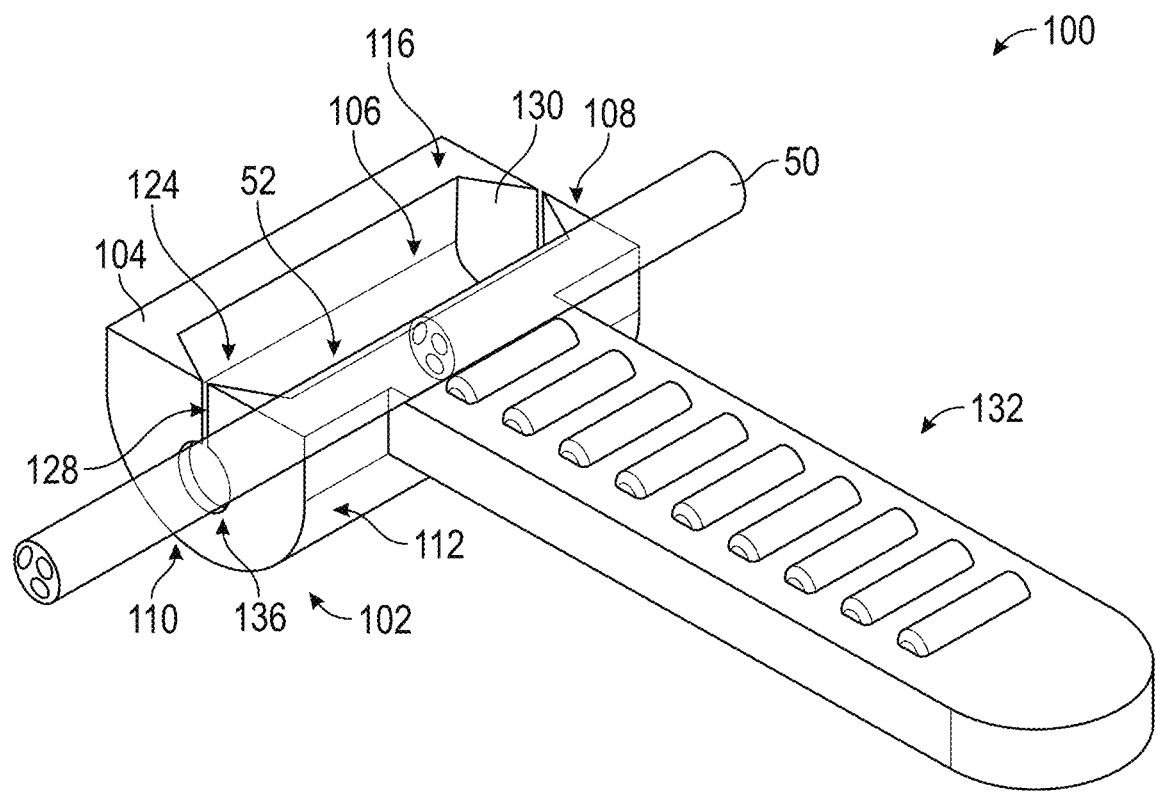
FIG. 1 illustrates a perspective view of an example of a nerve treatment device that may be used to deliver therapeutic solutions to an isolated segment of a nerve for nerve repair. The treatment device comprises an open configuration and slits and apertures in opposing sidewalls configured to receive and retain the nerve.

The device, method and kit contemplated herein are designed to rapidly repair and improve the recovery of injured peripheral nerves in an acute surgical setting. In some embodiments, a kit for nerve treatment (e.g., peripheral nerve treatment) may comprise three sterile solutions and, optionally, a device for focal, topical application (directly to the affected nerve) of the solutions. When applied sequentially according to the instructions for use, the solutions may comprise a therapeutic addition to surgical repair for patients with acute peripheral nerve injuries (PNI). The device may be used independently of the kit and/or the solutions and methods described herein for delivery of other therapeutic agents to a nerve and/or for isolating a nerve for other therapeutic treatments. The solutions may be used independently of the device and may be used for treatment of nerve injury according to methods and/or sequences other than those described herein. The methods and/or sequences described herein may be used with variations of the solutions described herein and/or may be used independently of the device described herein.

Components

Device

A nerve treatment device may be used in surgical settings to effectively isolate a segment of a nerve for treatment. The treatment device may be employed to uniformly and accurately apply PEG-fusion solutions to the isolated segment of the nerve at a nerve repair site (e.g., where the nerve is sutured together forming an anastomosis). The treatment device may accordingly be a delivery device. The treatment device may be included in a kit for nerve repair (e.g., a kit of solutions, such as for nerve fusion, described elsewhere herein) or may be provided as a stand-alone device. The treatment device may allow application of a PEG-fusion protocol, such as described elsewhere herein, in a reproducible fashion.

The treatment device can be made of any suitable material, including polymers, plastics, and/or rubbers. For example, the treatment device may be fabricated from one or more silicones (e.g., polydimethylsiloxane (PDMS) and/or plastics, such as polyether ether keytone (PEEK), polyurethane, polyethylene, polyolefin, polypropylene, polyether block amide, etc. The materials used may be medical grade plastics and/or silicones. In some embodiments, the device or portions thereof may be transparent or partially transparent to allow for visual inspection of the treated nerve within the device. The device may be disposable (e.g., configured for single-use) or may be reusable. The device may be sterilizable by conventional means (e.g., ozone, UV, autoclaving, etc.). The device may be fabricated by any suitable means, such as injection molding or compression molding. In some embodiments, the device may be fabricated as a single integral unit. In other embodiments, the device may comprise separately fabricated components which are subsequently coupled together (e.g., glued together, molded together, and/or mechanically secured together). In some embodiments, some of the components may be reversibly attachable/detachable. Some of the components may be reusable and other components may be disposable.

In various embodiments, the device, or portions of the device, may have a durometer between approximately 20-40 D. The durometer may be relatively low to prevent damage to the treated nerve. In some embodiments, the durometer may vary across different portions of the device. For instance, portions of the device that come into physical contact with and/or hold the nerve may be softer than other portions of the device. In some embodiments, the durometer of the device can be modulated by altering the concentration of the polymer and/or a crosslinking agent during fabrication. In some embodiments, the concentration can be variable across different portions of the device to produce a variable durometer. The flexibility of the device at various portions may depend on a combination of the durometer of the material and the dimensions of the portion.

In various embodiments, the treatment device may be a solid, non-articulating device that creates a temporary fluid containment field around the anastomosis between the proximal and distal ends of the nerve after suturing. The treatment device may be configured to prevent unnecessary exposure of surrounding tissues to a therapeutic agent, such as a PEG solution, during the administration of the agent to the nerve such that the device enables localized drug delivery. In some embodiments, the treatment device can be configured to perform no therapeutic action and may be only functional to temporarily contain a therapeutic solution around the nerve. The treatment device may allow controlled delivery and removal of a series of therapeutic solutions according to a sequence of administration. The treatment device may be in contact exclusively with the treated tissue (nerve). The device may be placed in contact with the treated tissue for only a short duration (e.g., 1-10 minutes). The device may be used for only a portion of the surgical or therapeutic procedure. The device need not be left implanted in the body. The device can be used to protect uninjured nerve segments and surrounding tissues from exposure to PEG during a fusion procedure. The device design may provide ease of use and may minimize disturbing the pre- and post-PEG-fused nerve during the surgical operation.

FIG. 1 illustrates a perspective view of an example of a nerve treatment device 100, which may be configured as delivery device for delivering a therapeutic solution (e.g., a PEG fusion solution) to a nerve. FIG. 1 includes examples of suitable, but non-limiting dimensions (in mm) for various portions of the treatment device 100. The treatment device 100 may generally comprise a body 102 having a sidewall 104. The sidewall 104 may be integral throughout the body 102 or may comprise multiple components coupled (e.g., attached) to one another. The sidewall 104 may define a containment chamber 106 having a void volume formed within the body 102. The containment chamber 106 may be configured to enclose or partially enclose a length or segment of a nerve 50 ("enclose" may be used herein to refer to any degree of enclosure). For example, the containment chamber may circumferentially surround the nerve by approximately 180 degrees, 270 degrees, 360 degrees, or any degree in a range defined there between. The containment chamber 106 may be configured to contain a volume of solution (e.g., a therapeutic solution) around or partially around the enclosed segment of the nerve 50. The body 102 may be configured to surround or partially surround the segment of the nerve 50 and to create a containment chamber 106 having a sufficient or precise volume to contain a desired amount of solution. The body 102 and containment chamber 106 may comprise dimensions configured to enclose a specific length of a nerve 50 and/or may be configured to enclose a nerve 50 having a specific diameter. The shape, dimensions, and/or material properties of the body 102 may be configured to stably enclose a desired length and size of nerve while generally minimizing the outer profile of the body 102 so as to facilitate easy insertion, removal, and/or manipulation of the device 100 within an in vivo space of the body. For instance, the body 102 may be configured to help separate the target segment of the nerve 50 from surrounding connective tissue. In some implementations, a user (e.g,. physician) may select from various sized devices 100 depending on the particular nerve to be treated. In some embodiments, kits may provide a plurality of devices 100 to select from which may vary in size and/or be designated for treatment of specific nerves.

The body 102 may generally comprise a left endwall 108, a right endwall 110, and an intermediate body 112 extending between the left endwall 108 and the right endwall 110. The body 102 may define a longitudinal axis extending from the left endwall 108 to the right endwall 110, generally in the direction the nerve 50 to be treated is to be aligned. The body 102 may comprise a lower body 114 having a top surface 116. The top surface 116 comprises an access area 118 through which the segment of the nerve 50 or at least a portion thereof may be received into the containment chamber 106. The access area 118 may comprise a width transverse to the longitudinal axis and a length parallel to the longitudinal axis. The width and/or the length of the containment chamber 106 may be the greatest or maximized at the access area 124 such that the width and/or length remain constant and/or decrease as the depth of the containment chamber 106 increases from the access area 124 downward. In some embodiments, such as that shown in FIG. 1, the body 102 may be configured as an open bath in which the treatment device 100 is configured to be used such that the lower body 114 is substantially oriented so that the top surface 116 faces upward and gravity substantially retains the solution within the containment chamber. The containment chamber 106 may be configured such that the segment of the nerve 50 may be entirely disposed within the void volume of the containment chamber 106 (e.g., the segment may be entirely submerged in solution) or the segment may be configured to be only partially disposed within the containment chamber 106 such that a top portion of the nerve 50 extends upward beyond the top surface 116. The volume within the containment chamber 106 may be configured to submerge the segment of the nerve 50 without being filled to the top surface 116. Open bath configurations may be especially advantageous for easy placement and withdrawal of a nerve 50 from a treatment device.

In other embodiments, the body 102 may be configured as a closed bath, as described elsewhere herein, comprising a lower body 114 and an upper body 120. The lower body 114 and the upper body 120 may cooperate to form a containment chamber 106 that substantially encloses the entire circumference of the segment of the nerve 50. In some implementations, closed bath embodiments may be oriented in any direction during use (e.g., the lower body 114 may be partially or entirely oriented above the upper body 120). The lower body 114 and upper body 120 may form a fluid seal that retains the solution within the containment chamber 106.

The left endwall 108 and/or the right endwall 110 of the body 102 may comprise substantially flat outer surfaces, as shown in FIG. 1. The left end wall 108 and the right endwall 110 may each comprise an aperture 126 extending through the sidewall 104 from an outer surface of the body 102 to an inner surface of the body 102 defining the containment chamber 106. The apertures 126 may comprise generally circular cross-sections or cross-sections of any suitable shape. The apertures 126 may be configured to receive the nerve 50 into the containment chamber 106. In some embodiments, the apertures 126 may be disposed within the sidewall 104 such that the circumference or periphery of the apertures 126 do not intersect the top surface 116. The left end wall 108 and the right endwall 110 may each comprise a thin slit 128 extending from the circumference of the aperture 126 to the top surface 116. The slits 128 may extend in a substantially vertical direction. The slits 128 may allow the sidewall 104 of the body 102 along opposite sides of the slits 128 to be biased away from each other (e.g., flexed apart) so that the nerve 50 may be received from the top surface 116 through the slits 128 and into the apertures 126.

In some embodiments, the sidewall 104 may comprise a tapered or decreasing thickness toward the slits 128. For instance, the thickness of the sidewall 104 may decrease as the sidewall 104 extends from a front side of the intermediate body 112 to the slit 128 and/or the thickness of the sidewall 104 may decrease as the sidewall 104 extends from a rear side of the intermediate body 112 to the slit 128, as shown in FIG. 1, where both front and rear sides of the slits 128 comprise portions of the sidewall 104 having tapered diameters. The end-walls 108, 110 of the containment chamber 106 can be designed with convening blades or flanges 130 that allow for a range of diameters of nerve to be placed within the device. The one or more flanges 130 may be formed from the sidewall 104. The flanges 130 may be configured to be flexed inward toward the containment chamber 106 and/or outward away from the containment chamber 106. Each flange 130 may have a distal edge forming the edge of the slit 130 and may have a proximal end near where the sidewall 104 begins to bend. The rate of taper when present may be constant, forming substantially triangular flanges 130 as shown in FIG. 1, or may be higher near the proximal end. In some embodiments, the sidewall 104 may be shaped into a flexible hinge (not shown) at a proximal end of the flange 130, such as a divot formed into the sidewall 104, which facilitates bending of the flange 130. The flange 130 may have a constant diameter or a decreasing diameter distal to the hinge. In some embodiments, the flange 130 may be configured to only bend in one direction or to bend more readily in one direction than the opposite direction. For instance, the flange 130 may be configured to bend inward toward the containment chamber 106, but may be configured not to bend or be less prone to bend outward away from the containment chamber 106.

In some embodiments, the aperture 126 may serve as a hinge and the portion of the body 102 on a first side of the hinge (e.g., a front portion) may be configured to bend away from the portion of the body 102 on a second opposing side of the hinge (e.g., a rear portion). For instance, with respect to FIG. 1, the front portion may be bent away from the rear portion such that the width of the slit 130 increases the greatest where it intersects the top surface 116 and increases the least where the slit 130 intersects the aperture 126. The strain may be distributed throughout the sidewall 104 but may be concentrated along a bottom portion of the body 102 substantially opposite the top surface 116. In some embodiments, the body 102 may be configured to bend in one or more directions, including any of the motions described herein.

The slits 128 may comprise opposing edges (e.g., front and rear edges) through which the nerve 50 is configured to pass between when the opposing edges are biased apart. The distal edges of opposing flanges 130 may form the opposing edges of the slit 128. In some embodiments, the opposing edges of the slit 128 may be contact or touch each other in an unbiased configuration such that the slit 128 has a width of approximately 0 mm in the unbiased configuration. In some embodiments, the slit 128 may have a width between the opposing edges of no greater than approximately 0.01 mm, 0.02 mm, 0.03 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm, or 3.0 mm. The width of the slit 128 may be dimensioned such that the surface tension of the solution contained within the containment chamber 106 prevents the solution from leaking through the slit 128 in an unbiased configuration or such that the leakage is minimal and/or negligible. In some embodiments, the opposing edges of the slit 128 may overlap in an unbiased configuration. For instance, the rear flange 130 may sit inward of the front flange 130 or vice-versa. The edges may overlap by at least about 0.01 mm, 0.02 mm, 0.03 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1.0 mm, 1.5 mm, 2.0 mm, or 3.0 mm. The overlap may prevent or inhibit leakage of fluid from the containment chamber 106. The slits 130 may comprise a length that is at least about 0.1 mm, 0.2 mm, 0.3 mm, 0.4 mm, 0.5 mm, 0.6 mm, 0.7 mm, 0.8 mm, 0.9 mm, 1 mm, 1.25 mm, 1.5 mm, 1.75 mm, 2.0 mm, 2.5 mm, or 3.0 mm.

In some implementations, a user may insert the target segment of the nerve 50 into the treatment device 100 (into the apertures 126) by using tools (e.g., tweezers, forceps, or other surgical instruments) and/or fingers to bias apart the opposing edges of the slits 128 in a manner as described elsewhere herein. In some implementations, the slits 128 may be sufficiently biased such that a sufficient gap or space may be established allowing the nerve 50 to be received through the slit 128 without contacting the edges of the slit 128 or with only non-incidental contact, such that the edges do not exert any significant friction or other forces on the nerve 50 during insertion. In some implementations, the body 102 may be sufficiently soft and flexible, particularly along the edges of the slits 130, such that the force imparted to the slit 130 by contact with the nerve 50 biases or facilitates in the biasing apart of the edges without imposing damage or injury to the nerve and/or without undoing or interfering with an anastomosis in the nerve 50. The nerve 50 may be grasped using tools (e.g., tweezers, forceps, or other surgical instruments) and/or fingers during the insertion. In some implementations, the nerve 50 may be inserted into the left and right apertures 126 sequentially, in any order. In some implementations, the nerve 50 may be inserted into the left and right apertures 126 substantially simultaneously. In various embodiments, the treatment device 100 may be designed without any articulating components, as in the device 100 illustrated in FIG. 1. The lack or minimization of articulating components avoids any areas in which a nerve or other sensitive tissue may be pinched between parts during operation, which may injure or damage the tissue. The use of a flexible body 102 (e.g., fabricated from lower durometer silicone) may advantageously provide dynamic properties to the treatment device 100 without articulation.

The apertures 126 may comprise diameters that are approximately equal in diameter to the diameter of the target nerve 50. The apertures 126 may be configured to form a fluid seal around the circumference of the nerve 50. In some embodiments, the diameter of the apertures 126 may be slightly less than a diameter of the nerve 50. For instance, the diameter may be at least approximately 90%, 95%, 96%, 97%, 98%, or 99% the diameter of the nerve 50. The sidewall 104, at least around the apertures 126, may be sufficiently compliant such that the apertures 126 are configured to accommodate the slightly larger nerve 50. Biasing apart the opposing edges of the slit 130 may increase the effective diameter of the aperture 126. In some implementations, the flanges 130 may be biased inward or outward to increase the effective diameter of the aperture 126. In some embodiments, the aperture 126 or a portion thereof (e.g., the portion closes to the slit 128) may be disposed on the flexible flange 130 allowing greater expansion of the diameter of the aperture 126. The body 102 may be sufficiently soft and flexible such that the apertures 126 do not exert high enough pressure on the nerve 50 to damage or injure the nerve 50 or to undo or interfere with an anastomosis in the nerve 50. The flanges 130 may be configured to exert a gentle compressive pressure against the nerve 50 forming a compressive fluid seal at partially around the circumference of the nerve 50. In some embodiments, the diameter of the apertures 126 may be slightly larger than that of the target nerve 50. For example the diameter may be no greater than approximately 101%, 102%, 103%, 104%, 105%, or 110% the diameter of the target nerve. The surface tension of the solution contained within the containment chamber 106 may prevent the solution from leaking through the aperture 126 in an unbiased configuration or prohibit leakage such that it is minimal and/or negligible.

In some embodiments, the range of nerve diameters may be between 1-4 mm, between 4-8 mm, between 8-12 mm, or overlapping ranges or ranges there between. The treatment device 100 may be manufactured in several different sizes to accommodate different ranges of nerve diameters. The treatment device 100 may be applied to any suitable nerve. For example, the treatment device 100 may be applied to a digital nerve (about 1-2 mm). In another example, the device may be applied to the median nerve in the wrist (about 5-7 mm).

In some embodiments, the body 102 or even the entire treatment device 100 may be symmetric about a midline separating a left half and right half of the body 102 or device 100. In some embodiments, the left end wall 108 may be a mirror image of the right endwall 110. For instance the, apertures 126 may be aligned along a longitudinal axis of the device 100. extending from the left end wall 108 to the right endwall 110 such that the nerve 50 may be positioned in the apertures 126 and the distribution of the void volume of the containment chamber 106 around the segment of the nerve 50 is uniform as the nerve 50 extends from the left end wall 108 to the right endwall 110. The slits 128 may be aligned along a longitudinal axis of the device 100. In some embodiments the apertures 126 may not impart any significant tension on the nerve 50, such that the nerve 50 is freely moveable (e.g., translatable in a left or right direction and/or rotatable) when disposed within the apertures 126. The apertures 126 may generally maintain the isolated segment of the nerve 50 within the containment chamber 106. In some embodiments, the apertures 126 may be configured in a non-biased configuration to exert a nominal amount of tension on the segment of the nerve 50 positioned within the containment chamber 106. The tension may be great enough to hold or secure the nerve 50 within the treatment device 100. For instance, the tension may be configured to prevent or prohibit the nerve 50 from sliding in a right or left direction through the apertures 126 of the device. The tension may be configured to remove any slack from the segment of the nerve 50 disposed within the containment chamber 106. The tension may prevent the nerve 50 from freely rotating within the apertures 126.

In some embodiments, the treatment device 100 may be configured to position the nerve 50 within the containment chamber 106 such that the nerve 50 is suspended between the right and left apertures 126 and the contained solution may fill in a portion of the void volume between a bottom surface of the containment chamber 106 and the isolated segment of the nerve 50. In some embodiments, the contained solution may be filled to a level within the containment chamber 106 such that it surrounds the entire circumference of the isolated segment of the nerve 50 between the left and right apertures 126. In other embodiments, the apertures 126 may be positioned in the sidewall 104 of the left and right endwalls 108, 110 such that a portion of the edge or circumference of the aperture 126 is coplanar with a portion of a surface of the containment chamber 106. In such embodiments, the isolated segment of the nerve 50 may be positioned to sit against a surface of the containment chamber 106 (e.g., along a bottom surface of the containment chamber 106) along a length of the intermediate body 112. In such embodiments, the body 102 may be used to support the weight of the nerve 50 between the right and left apertures 126, which may allow the body 102 to be configured to exert less friction on the nerve 50 via the apertures 126. In some implementations, the contained solution may or may not wet the surface of the nerve 50 configured to be disposed against inner surface of the containment chamber 106.

In some embodiments, the apertures 126 may be positioned above (closer to the top surface 116) than a bottom surface or floor of the containment chamber 106, such that the lowest point of the apertures 126 is above the lowest point of the floor. The internal floor of the containment chamber 106 can be beveled or curved such that the nerve 50 is not under tension when placed in the treatment device 100. The floor may rise to meet the aperture 126 so that the nerve 50 may be disposed in a somewhat curved orientation (e.g., a subtle U-shaped orientation) when rested against the floor of the containment chamber 106. The variable depth floor may fully support the isolated segment of the nerve 50 along the length of the intermediate body 112 but may be configured to position an intermediate portion of the nerve 50 (e.g., an anastomosis) in a lower portion of the containment chamber 106. The variable depth may allow the contained solution to cover, submerge, and/or be more concentrated near the intermediate portion while keeping the contained solution away from the apertures 126 and/or slits 128 or minimizing the amount of solution that is disposed adjacent the apertures 126 and/or slits 128. Such a configuration may allow the apertures 126 and/or slits 128 to comprise larger dimensions that exert less friction, tension, or other forces on the nerve 50, since fluid containment may be less a concern. In some embodiments, the intermediate body 112 and/or the internal chamber 106 may comprise a length along the longitudinal axis that is at least approximately 5 mm, 10 mm, 15 mm, 20 mm, 25 mm, 30 mm, 35 mm, 40 mm, 45 mm, or 50 mm.

In some embodiments, the body 102 may comprise a cross-sectional profile traverse to the longitudinal axis which has a circular, semi-circular, round, rectangular, square, or polygonal shape or any other suitable shape. In some embodiments, the shape may be a partial stadium or obround shape as shown in FIG. 1. In some embodiments, the outer periphery of the cross-section may substantially match the shape of the inner periphery, which defines the containment chamber 106. The sidewall 104 may have a generally uniform thickness, at least along the length of the intermediate body 112. The cross-sectional shape of the containment chamber 106 may be configured to minimize the surface area-to-volume ratio of the containment chamber. In some embodiments, the bottom surface or floor of the containment chamber may be round along the transverse axis. The floor may dip or deepen toward the middle of the floor in the transverse direction, which may help situate the isolated segment of the nerve 50 and/or may at least partially cradle the nerve 50 providing additional support. The profile of the outer surface of the body 102 may generally be round or have rounded edges to make the treatment device 100 relatively atraumatic for interfacing with body tissue. In some embodiments, the outer bottom surface of the body 102 may be flat or have a flattened surface for providing stability. For instance, the flat surface may allow the body to stably rest on another flat surface. In some embodiments, the body 102 may be symmetric about a midline extending between a front portion and rear portion of the body 102.

In various embodiments, the treatment device 100 may comprise a handle 132 for handling and/or placing the device 100. The handle 132 may extend from the body 102. In some embodiments, the handle 132 may extend from the intermediate body 112, as shown in FIG. 1. The handle 132 may bisect the body 102. The handle 132 may comprise a generally elongate body having a proximal end and a distal end. The proximal end of the handle 132 may be connected to or integral with the body 102. The distal end of the handle 132 may be vertically aligned with the proximal end, as shown in FIG. 1, or may be positioned above or below the proximal end, as described elsewhere herein. The distal end of the handle 132 may be horizontally aligned with the proximal end, as shown in FIG. 1, or may be positioned to the left or the right of the proximal end. The length of the elongate body of the handle 132 may be transverse to the longitudinal axis of the body 102. A top surface of the handle 132 may be flush with the top surface 116 of the body. In some embodiments, the length of the handle may be at least about 5 mm, 10 mm, 15 mm, 20 mm, 25 mm, or 30 mm. The placement handle 132 can be designed for gripping with a standard forceps, tweezers, or other surgical tool. In some embodiments, the handle 132 is configured for gripping by the user's fingers and/or hand. In some embodiments, the handle 132 comprises a textured surface which facilitates gripping. The surface of the handle 132 may be textured on any one or more of its surfaces (e.g., upper, lower, left, right). For instance, the handle 132 may comprise ridges, as shown in FIG. 1, grooves, bumps, a knurled surface, etc. In some embodiments, the handle 132 may comprise indentations or depressions specifically configured for corresponding to a specific surgical tool. In some embodiments, the handle 132 is formed integrally with the body 102. In some embodiments, the handle 132 is coupled to the body 102 (e.g. glued or mechanically attached). The handle 132 may comprise the same or different materials than the body 102. In some embodiments, the handle 132 may be more rigid and/or may comprise more rigid materials than the body 102. In some embodiments, there may be more than one handle 132 (e.g., 2, 3, 4 or more handles). The handles disclosed on the various embodiments of the treatment devices described herein may generally be interchanged with one another and/or various features of the described handles may be interchanged.

FIGS. 2-11E illustrate further examples of various embodiments of the treatment device 100. The various features of the disclosed examples of the treatment devices 100 may be combined or switched, unless not possible to do so. For instance, in some embodiments, the treatment device 100 can envelope the nerve at the site of anastomosis, with a wiper-style seal on each end, such as described with respect to FIG. 1. In some embodiments, the wiper-style seal may be formed from one more flanges 130 or flexible wiper blades as described elsewhere herein. Corresponding numerals (e.g. 130, 230, and 330) may reference corresponding features described elsewhere with respect to another figure or embodiment.

Figure 2:
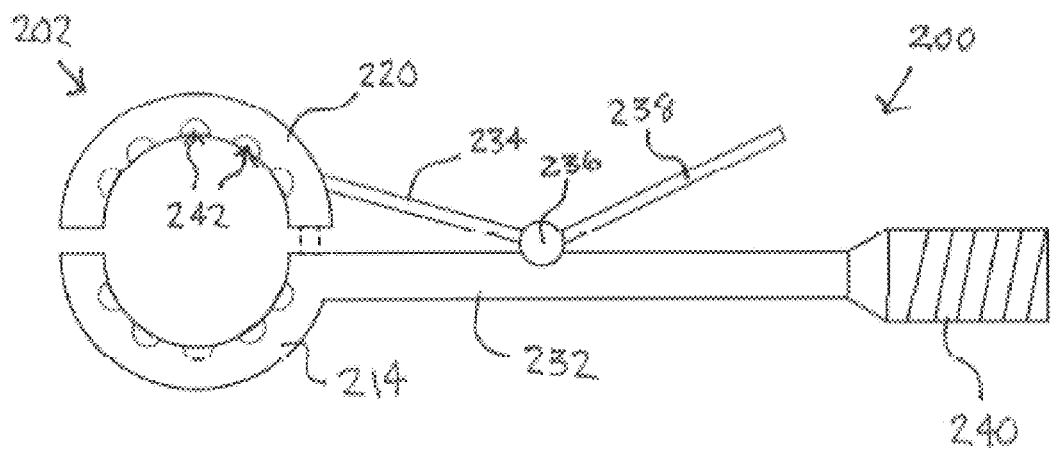
FIG. 2 schematically illustrates another example of a nerve treatment device, which has separable lower and upper bodies and fluid irrigation holes.

In various embodiments, the body may comprise a lower body and an upper body as described elsewhere herein. FIG. 2 schematically illustrates an example of a treatment device 200 comprising lower and upper bodies 214, 220. The lower body 214 and the upper body 220 may cooperate to enclose an entire circumference of the isolated segment of the nerve 50, as shown in FIG. 2. The lower body 214 and the upper body 220 may each comprise approximately half the circumference and half the volume of the containment chamber 206. In some embodiments, the upper body 220 may not comprise any portion of the void volume of the containment chamber 206 but may serve to seal the top surface 216 of the lower body 214 to fully enclose the containment chamber 206. In some embodiments, as shown in FIG. 2, the upper body 220 may be indirectly coupled to the lower body 214 by a connecting arm 234. The connecting arm 234 may be coupled to the handle 232 at a hinge 236. The hinge 236 may be positioned significantly away from the body 232 to avoid pinching the nerve or any surrounding tissue. A lever 238 may extend from the hinge 236 and allow the user to articulate the upper body 220 between closed (e.g., sealed) and open configurations. In some embodiments, the lever 238 may be an extension of the connecting arm 234. The lever 238 may extend in a generally distal direction of the handle 232. The lever 232 may be actuated by one or more fingers of the user or by a tool.

In various embodiments, the body 202 of the treatment device 200 may be configured to deliver fluid (e.g., a therapeutic solution) into the containment chamber 206, particularly in embodiments comprising closed bath designs. The treatment device 200 may comprise one or more internal fluid channels extending through the body 202 and optionally the handle 232. The device 200 may comprise one or more fluid ports 240 extending from the body 202 or the handle 232 configured for the introduction of fluid into the containment chamber 206 and/or withdrawal of fluid from the containment chamber 206. In some embodiments, the fluid port 240 may comprise or may be coupled to a luer lock connector. The luer lock connector may be configured to readily engage and disengage a syringe.

The treatment device 200 schematically illustrated in FIG. 2 comprises a fluid port 240 extending from a distal end of the handle 232. The fluid port 240 illustrated in FIG. 2 comprises a luer lock connector that can be easily attached to successive syringes loaded with appropriate solutions, such as according to a PEG-fusion protocol, described elsewhere herein. The treatment device 200 can accordingly minimize or remove variability (e.g., in the volume) in the delivery of the solutions to the containment chamber. The treatment device 200 illustrated in FIG. 2 comprises a fluid channel extending from the fluid port 240, through the handle 232, and into the lower body 214. In some embodiments, the lower body 214 and/or the upper body 220 may be hollow and the interior(s) may form the fluid channel. The lower body 214 comprises one or more irrigation holes 242 fluidly connecting the fluid channel and the containment chamber 206. In some embodiments, the upper body 220 may comprise an internal fluid channel and one or more irrigation holes 242 fluidly connecting the fluid channel and the containment chamber 206, at least when in a closed configuration. The fluid channel of the upper body 220 may be placed into fluid communication with the fluid channel in the lower body 214 and/or handle 232 when the upper body 220 is positioned in a closed configuration such that fluid may flow from the lower body 214 and/or handle 232 into the upper body 220.

Figure 4A:
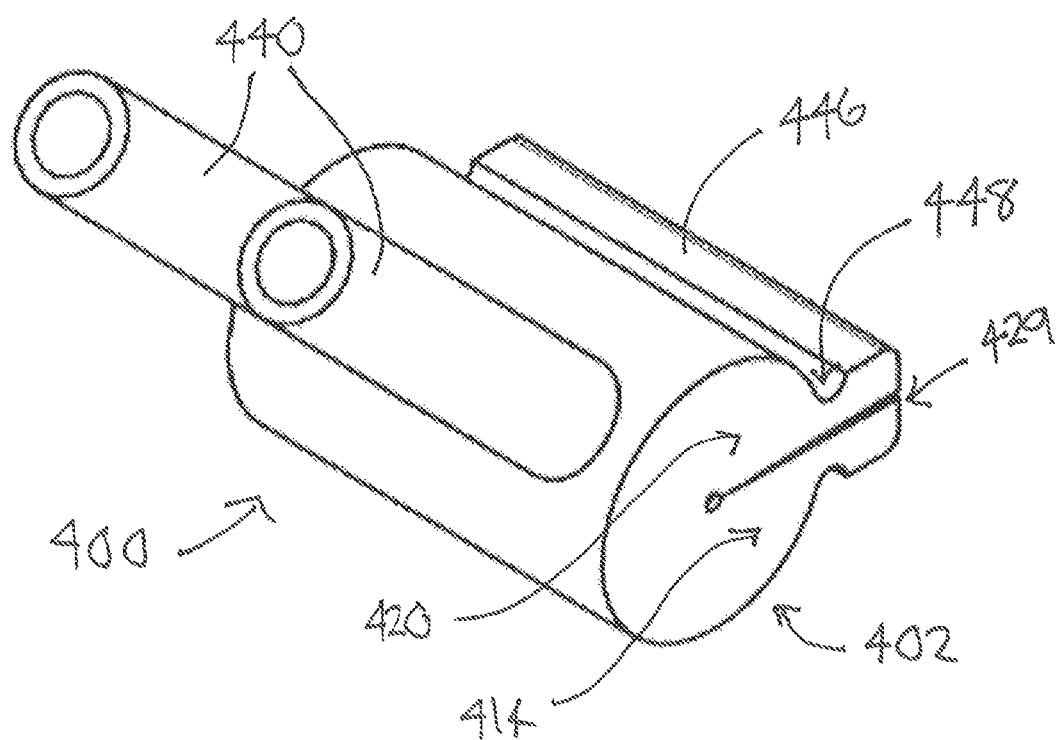
FIGS. 4A-4D schematically illustrate multi-perspective views of another example of a treatment device similar to that shown in FIGS. 3A-3E.

In some embodiments, the treatment device may have a split through it from the edge of a lip or flange extending along the length of the intermediate body to the center of a cylindrical portion or other-shaped intermediate portion of the body (e.g., to the containment chamber) to facilitate placement of the nerve 50 (see, e.g., FIG. 4A). The split may be formed by or similar to slits 130 and may effectively divide the body into portions corresponding to a lower body and an upper body. Once the nerve 50 is placed, the treatment device can be held together with a spring clip (e.g., a custom-fabricated spring clip) that can nestle into the channel between the lip and the cylindrical body. The device may have one, two, or more ports extending directly into the central cavity defining the containment chamber. The ports may be designed to facilitate interfacing with luer lock syringes, allowing for immersion of the nerve in solution (e.g., fusion solution), and rapid aspiration with saline after completion of the treatment, as described elsewhere herein.

Figure 3A:
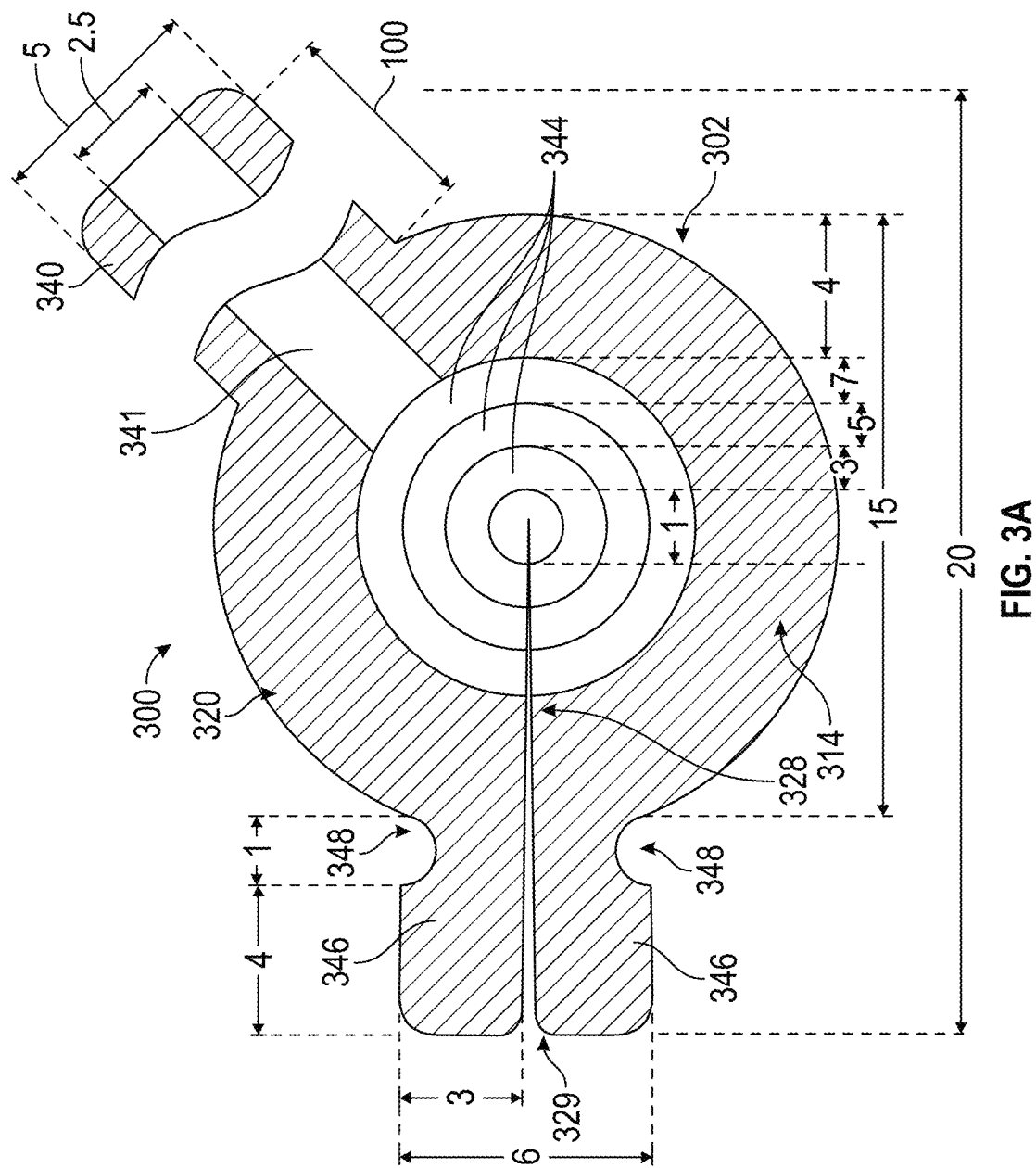
FIGS. 3A-3E schematically illustrate multi-perspective views of another example of a treatment device, which comprises integral upper and lower bodies separated by a split for receiving the nerve.
Figure 3B:
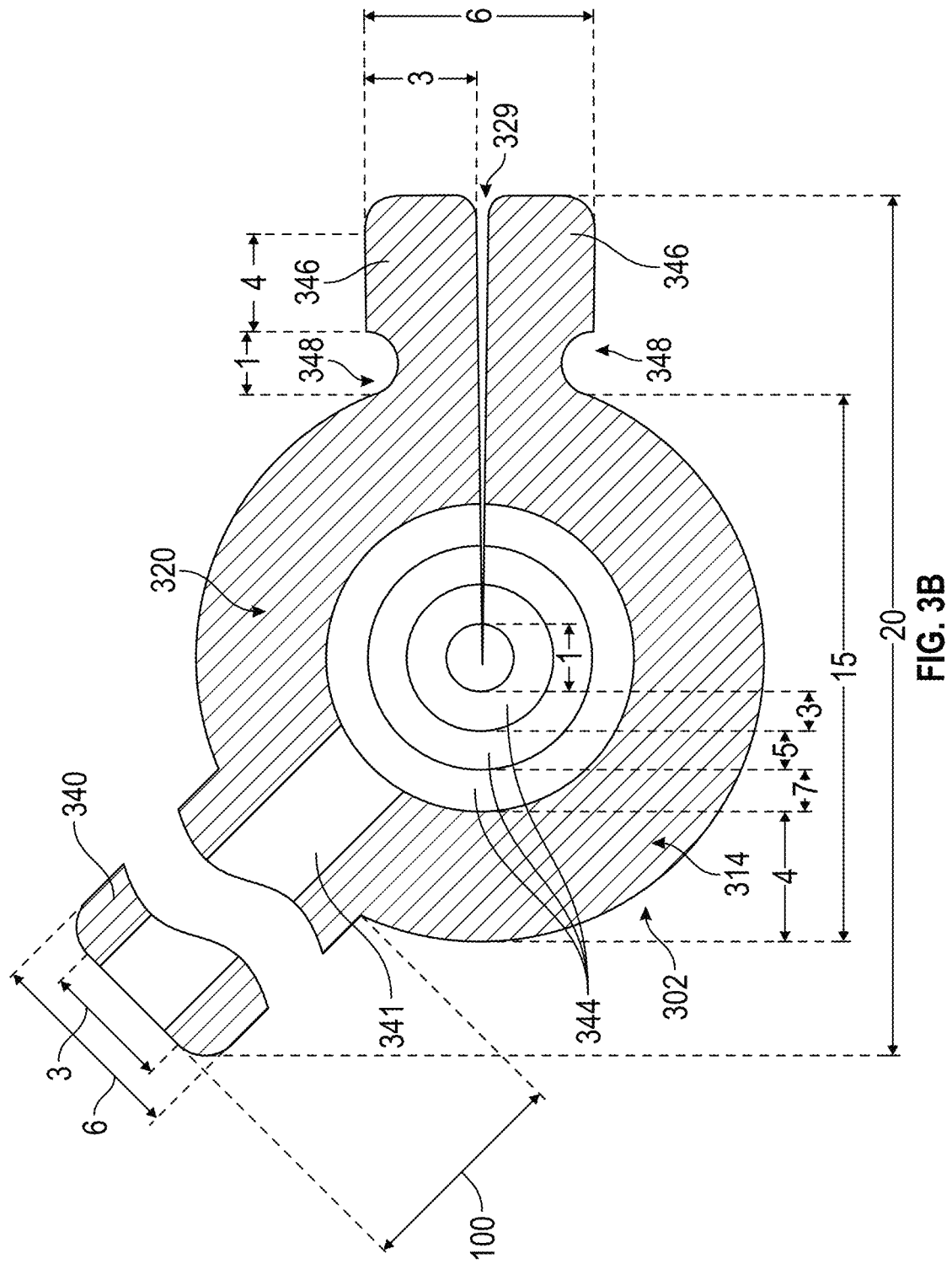
Figure 3C:
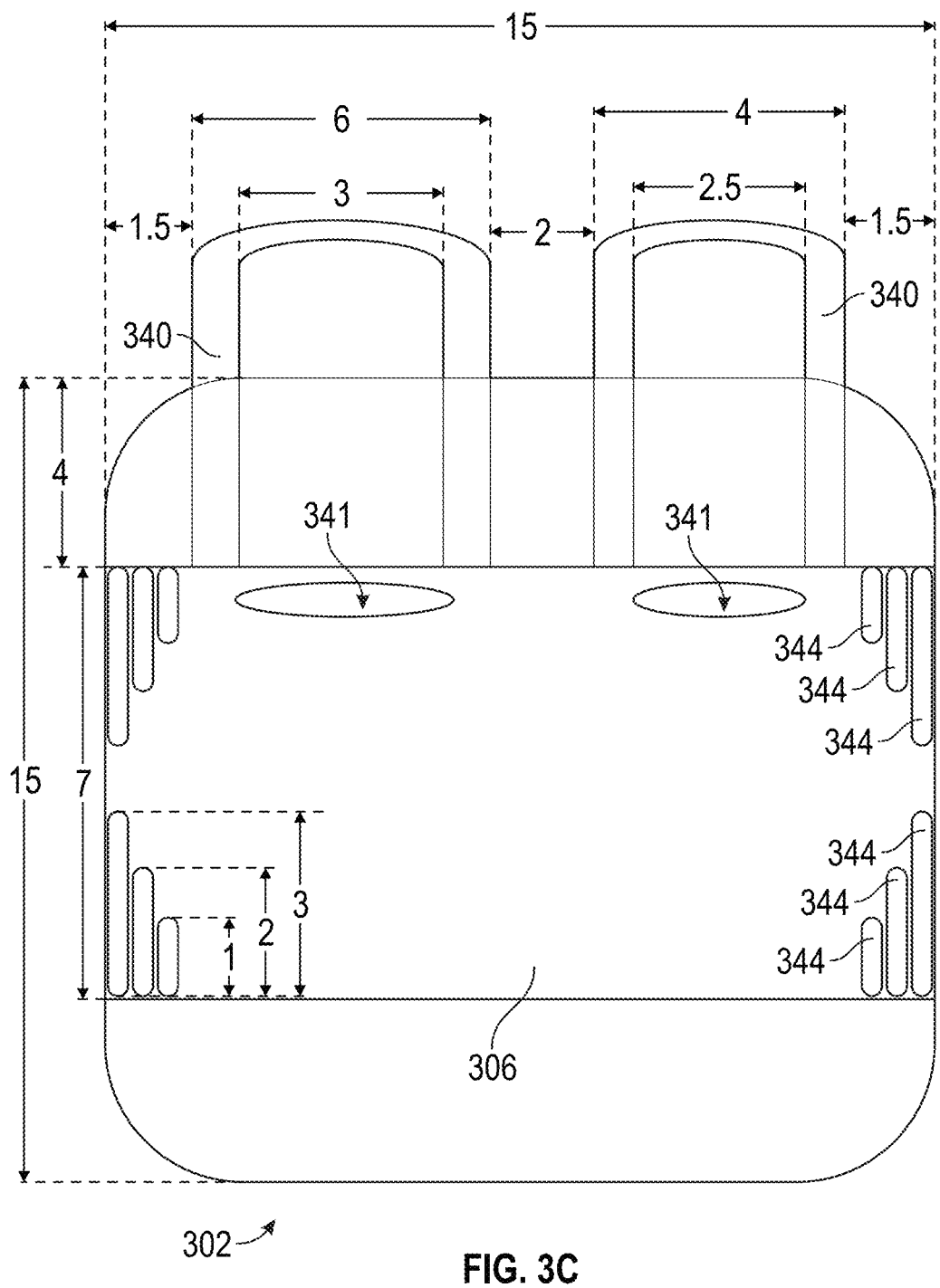
Figure 3D:
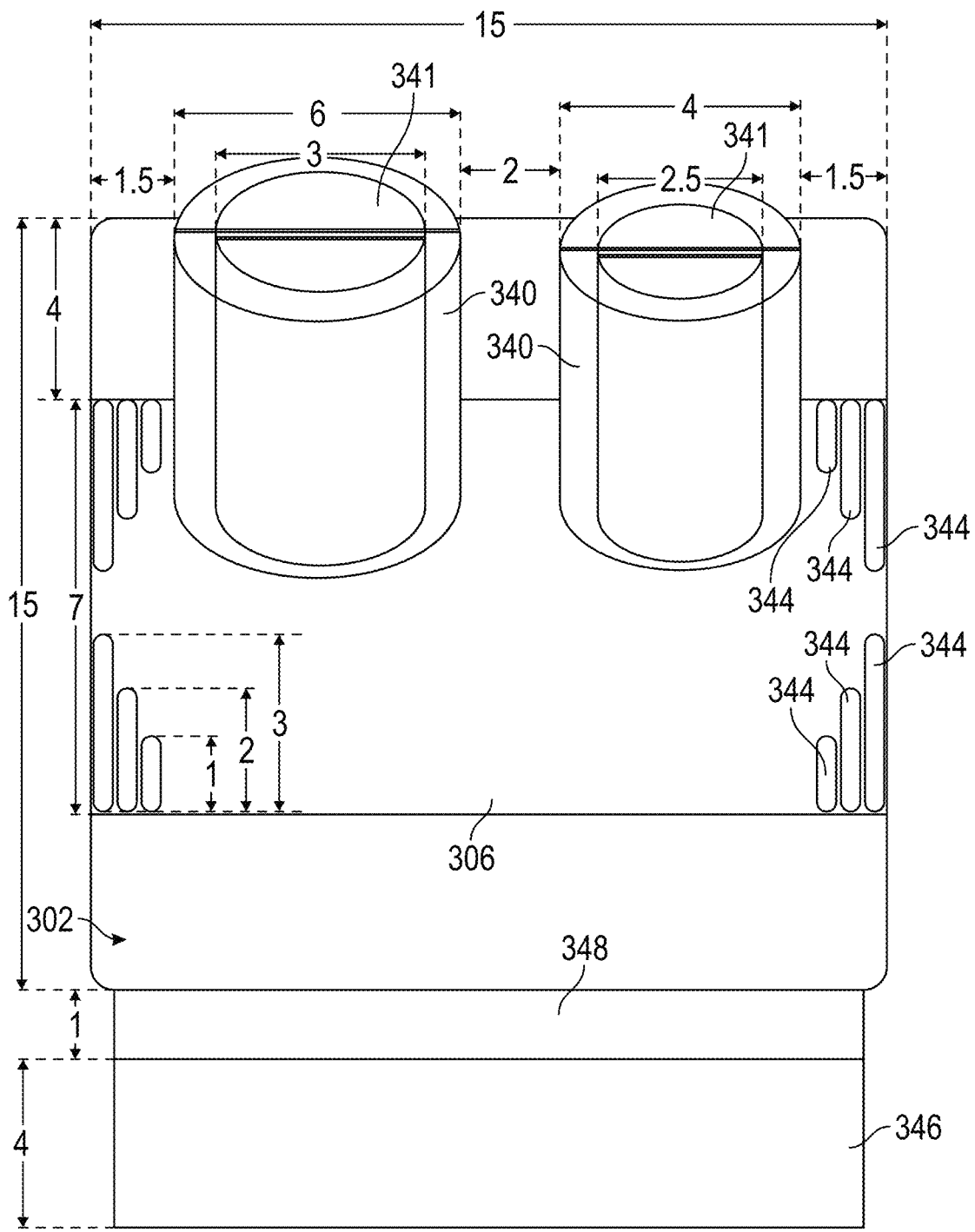
Figure 3E:
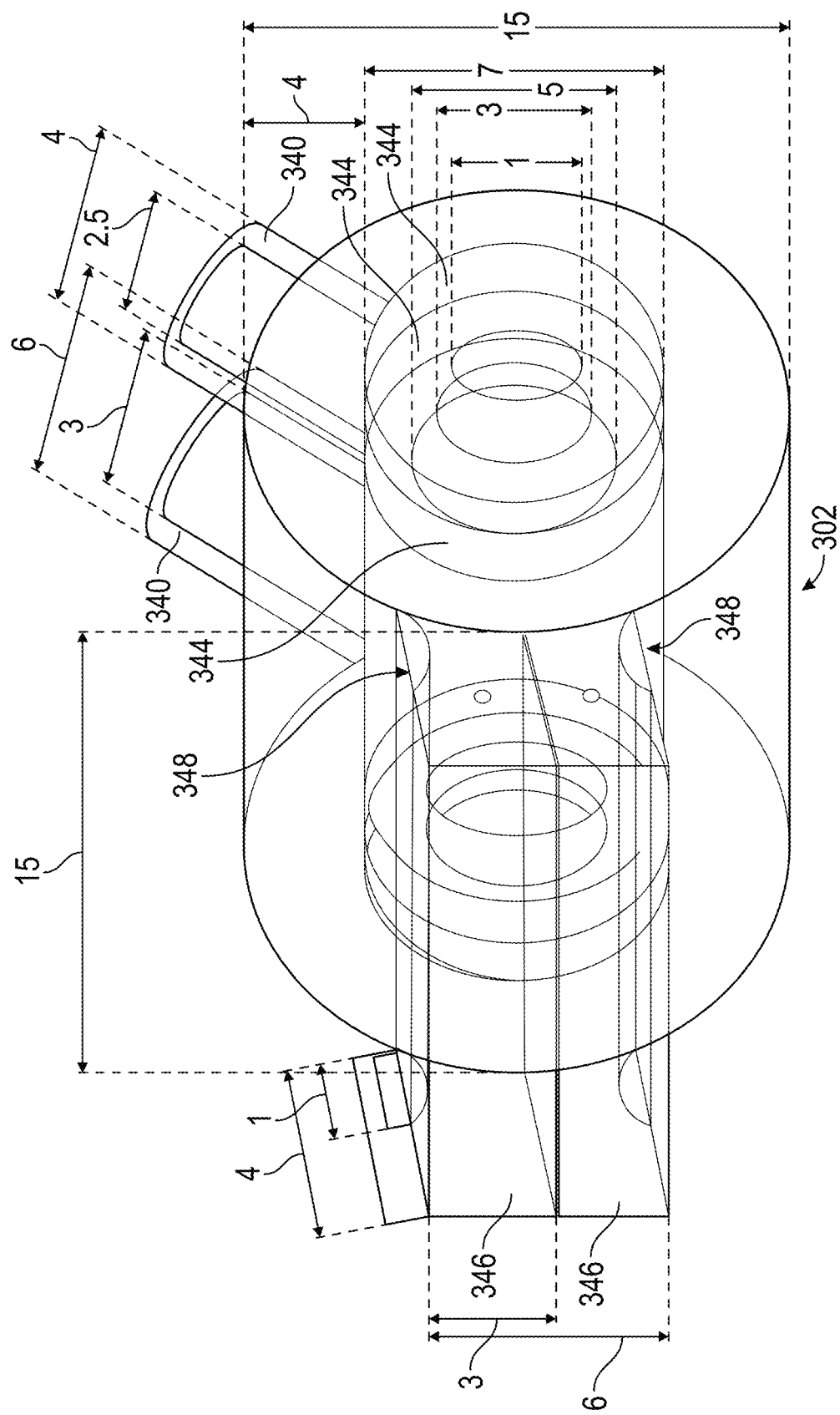

FIGS. 3A-3E schematically illustrate multi-perspective views of another example of a treatment device 300. FIGS. 3A-3E includes examples of suitable, but non-limiting dimensions (in mm) for various portions of the treatment device 300. FIG. 3A depicts a right cross-sectional view of the treatment device 300. FIG. 3B depicts a left cross-sectional view of the treatment device 300. FIG. 3C depicts a rear view of the treatment device 300. FIG. 3D depicts a front view of the treatment device 300. FIG. 3E depicts a perspective view of the treatment device 300. The treatment device 300 may comprise a generally cylindrical body 302 having a generally circular left endwall 308 and a generally circular right endwall 310 connected by a generally cylindrical intermediate body 312. The body 302 may enclose a generally cylindrical containment chamber 306. The left endwall 308 and the right endwall 310 may each comprise a generally circular aperture 326 opening into the containment chamber 306. The apertures 326 may be substantially centered within the endwalls 308, 310. The body 302 may comprise a split 329 extending longitudinally along the intermediate body 312. The split 329 may be coplanar with the longitudinal axis (it may not extend along the intermediate body 312 in a circumferential direction). The split may extend from an outer surface of the body 302 to the containment chamber 306 and may effectively divide or proportion the body 302 into a lower body 314 and an upper body 320. The lower body 314 and the upper body 320 may be joined (e.g., integral with one another) at a point of the body 302 circumferentially opposite the split 329. The upper body 314 and lower body may be biased apart from each other around this point. The split 329 may extend (e.g., in a radial direction) through each of the endwalls 308, 310 to merge with the apertures 326. The split 329 may form slits 328 in the endwalls 308, 310. Increasing the width of the split 329 between an edge of the lower body 314 and an opposing edge of the upper body 320 may place the treatment device 300 in an open configuration configured to receive the target nerve 50 through the split into the containment chamber 306 such that the nerve 50 extends through the right and left apertures 326. In some embodiments, the opposing edges (e.g., upper and lower edges) along the length of the split 329 may be brought into contact with each other placing the treatment device 300 into a closed configuration in which the body 302 is configured to enclose the entire circumference of the isolated segment of the nerve 50 within the containment chamber 306. In other embodiments, the opposing edges of the split 329 may be brought into close proximity to each other without establishing physical contact between the edges (e.g., within approximately 1 mm, 0.9 mm, 0.8 mm, 0.7 mm, 0.6 mm, 0.5 mm, 0.4 mm, 0.3 mm, 0.2 mm, 0.1 mm, etc.), creating a closed configuration in which substantially the entire circumference of the nerve 50 is enclosed.

In some embodiments, the treatment device 300 may comprise one or more inserts 344 configured to be positioned within the containment chamber 306 at left and right ends of the containment chamber 306. The inserts 344 may generally be ring-shaped or washer-shaped comprising a central aperture. The inserts 344 may generally comprise substantially flat left and right surfaces. The thickness of the inserts 344 may be less than a width of the annular flat surfaces from an outer circumference to an inner circumference. The inserts 344 may comprise the same and/or different materials as the body 302. The inserts 344 may comprise a stiffness that is the same as or less than that of the body 302. The inserts 344 may be grouped in pairs, each pair comprising identical inserts 344 configured to be positioned at the right and left ends of the containment chamber 306. At least one of the inserts 344 may be configured to form at least a portion of the left endwall 308. At least one of the inserts 344 may be configured to form at least a portion of the right endwall 310. The inserts 344 may each comprise a slit through its circumference configured to align with the slit 328 in the adjacent endwall 308, 310. Each pair of inserts 344 may comprise an outer diameter approximately equal to the diameter of the containment chamber 306 and an inner diameter configured to accommodate a nerve 200 of different sizes (e.g., 1 mm, 2 mm, 3 mm, 4 mm, 5 mm, 6 mm, etc.).

In some implementations, the selection of the appropriately sized insert 344 may adapt the treatment device 300 for treatment of different nerves (e.g., different diameter nerves). In some embodiments, the inserts 344 may be inserted into and coupled to an inner diameter of the containment chamber 306 (e.g., via adhesive). In some embodiments, the inserts 344 may be fabricated with the body 302. The inserts 344 may be arranged from outside to inside (from the endwalls 308, 310 inward) in order of increasing diameter of the central aperture of the insert 344. In some embodiments, all the inserts 344 (e.g., 2 pairs, 3 pairs, 4 pairs, 5 pairs, etc.) may remain in the containment chamber 306 and the inserts 344 which comprise smaller diameters than the isolated nerve 50 may conform to (e.g., bend outward around) the size of the nerve 50. Smaller nerves will encounter less resistance than larger nerves, as the smaller the nerve, the fewer number of inserts 344 the nerve is likely to deform. The increasing number of overlapping inserts 344 around the circumference of the nerve 50 may strengthen the fluid seal around the nerve 50. In some embodiments, the inserts 344 may be independently removable from the containment chamber 306. For example, the inserts 344 may comprise a frangible connection to the containment chamber 306 or may be cut away by a surgical instrument. In some implementations, a user may selectively remove inserts 344 which comprise apertures that are too small to receive the target nerve 50, leaving only the inserts 344 which are sufficiently sized to receive the nerve 50.

In some embodiments, the treatment device 300 may comprise one or more lips 346 extending longitudinally along an entire or partial length of the intermediate body 312. The lips 346 may be coplanar with the longitudinal axis (may not extend along the intermediate body 312 in a circumferential direction). The lips 346 may be positioned circumferentially adjacent the split 329. For instance, the split 329 may separate an upper lip 346 from a lower lip 346, as shown in FIGS. 3A-3E. The one or more lips 346 may each comprise a groove 348 extending longitudinally along an entire or partial length of the lips 346. In some embodiments, the grooves 348 may comprise a semicircular cross-section as shown in FIGS. 3A-3E. A groove 348 on an upper lip 346 may be longitudinally aligned above a groove 348 on a lower lip 346. The grooves 348 may be configured to receive, retain, and/or frictionally engage a portion of securing device (e.g., a spring clip) configured to secure the upper and lower lips 346 together. In some embodiments, the groove may abut the outer cylindrical surface of the intermediate body 312. Securing the upper and lower lips 356 together may place the body 302 in a closed configuration as described earlier, in which opposing edges of the split 329 are brought together or at least in which the width of the split 329 is minimized. In some embodiments, the body 302 may be configured such that the lower body 314 and the upper body 320 are in a closed position in an unbiased configuration. The lower body 314 and the upper body 320 may be pried apart (e.g., via lips 346) to place the body 302 into an open configuration for insertion of the nerve 50. In other embodiments, the lower body 314 and the upper body 320 may be naturally biased to an open configuration and the securing device may hold the body 302 in a closed position. The body 302 may be naturally biased to position the lower body 314 and the upper body 320 in a maximally separated state, a minimally separated state, or anywhere in between.

The treatment device 300 may comprise one or more fluid ports 340 configured for the delivery of fluid into and/or the removal of fluid from the containment chamber 306 as described elsewhere herein. The fluid ports 340 may be generally cylindrical in shape. The fluid ports 340 may comprise fluid lumens 341 extend directly into the containment chamber 306 as shown in FIGS. 3A-3E. The fluid lumens 341 may be substantially linear. The fluid lumens 341 may be generally cylindrical in shape. In some embodiments, as shown in FIGS. 3A-3E, the treatment device 300 may comprise two fluid ports 340. The fluid ports 340 may comprise identical or similar features or may comprise different features (e.g., shape, dimension, material properties). In some implementations, one fluid port 340 may be used for delivery of fluid into the containment chamber 306 (e.g., via a syringe) and the other fluid port 340 may be used for removal or aspiration of fluid from the containment chamber 306 (e.g., via a syringe or a vacuum line). The delivery and removal may occur sequentially and/or simultaneously. In some implementations, both fluid ports 340 may be used for delivery and/or removal. For example, two components of a therapeutic solution may be delivered separately through the fluid ports 340 into the containment chamber 306, sequentially and/or simultaneously. One or more of the fluid ports 340 may be circumferentially aligned along the outer circumference of the intermediate body 312 or may be circumferentially offset. The fluid ports 340 may be circumferentially offset from the lips 346 by any degree between 0 and 360 degrees (e.g., 30 degrees, 45 degrees, 60 degrees, 90 degrees, 120 degrees, 135 degrees, 165 degrees, 180 degrees, etc.). In some embodiments, the fluid ports 340 may be formed in one or more lips 346 and/or may extend from one or more lips 346.

In some embodiments, the treatment device 300 may comprise one or more handles similar to handle 132 or 232, as described with respect to FIGS. 1 and 2, respectively. In some implementations, the one or more lips 346 and/or the one or more fluid ports 340 may be effectively used as handles and may be configured to be grasped by surgical tools and or fingers as described elsewhere herein.

Figure 4B:
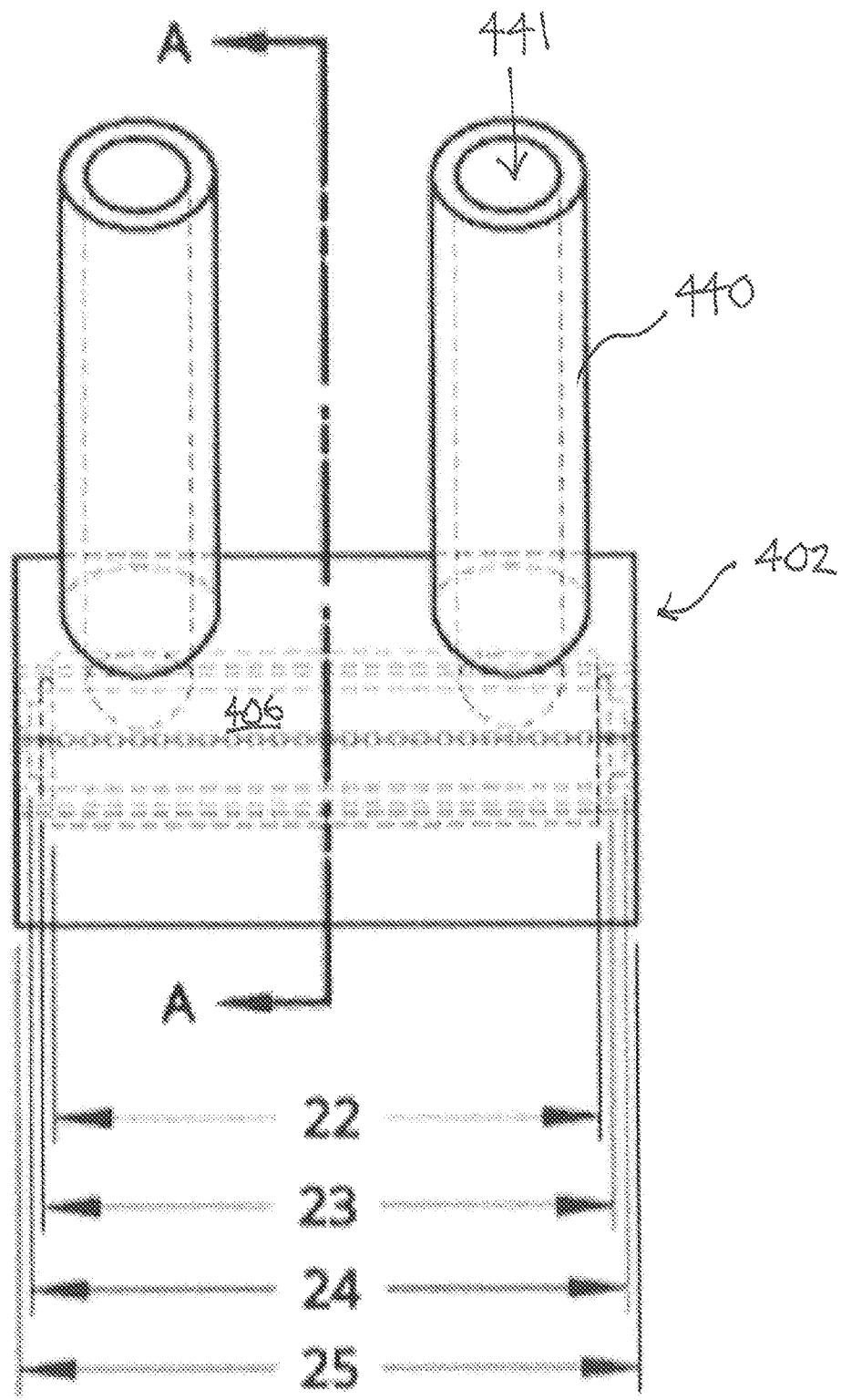
Figure 4C:
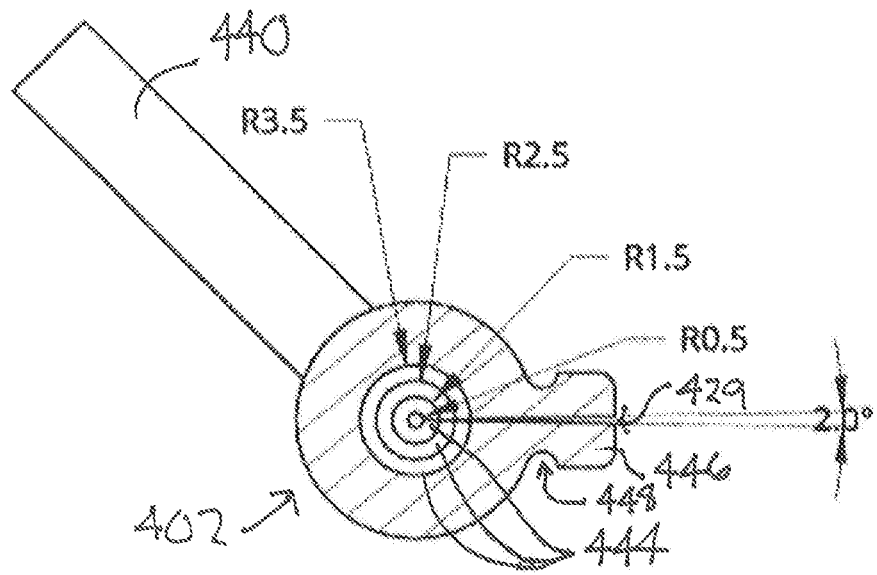
Figure 4D:
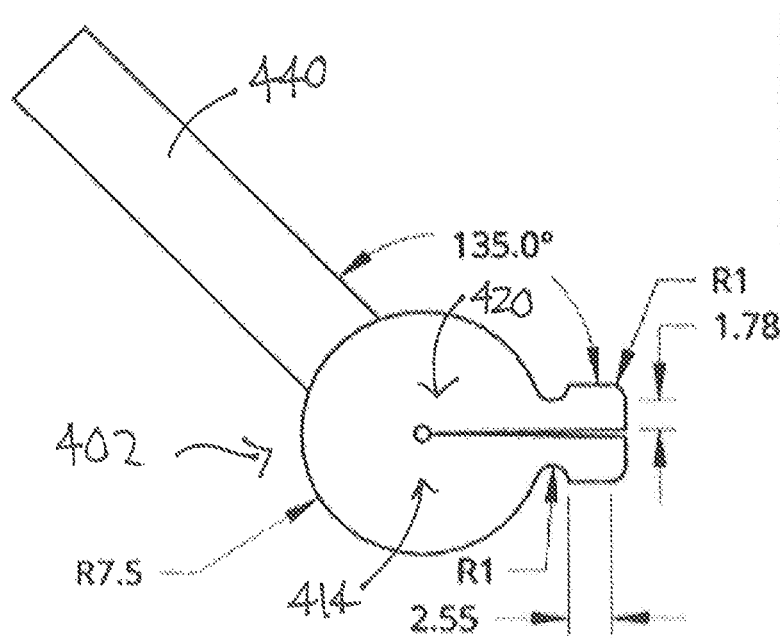

FIGS. 4A-4D schematically illustrate multi-perspective views of another example of a treatment device 400. FIGS. 4A-4D include examples of suitable, but non-limiting dimensions (in mm) for various portions of the treatment device 400. FIG. 4A depicts a perspective view of the treatment device 400. FIG. 4B depicts a front view of the treatment device 400. FIG. 4C depicts a cross sectional view of section A-A indicated FIG. 4B. FIG. 4D depicts a view of the left side of the treatment device 400. The treatment device 400 may comprise the same or similar features as treatment device 300.

Figure 5A:
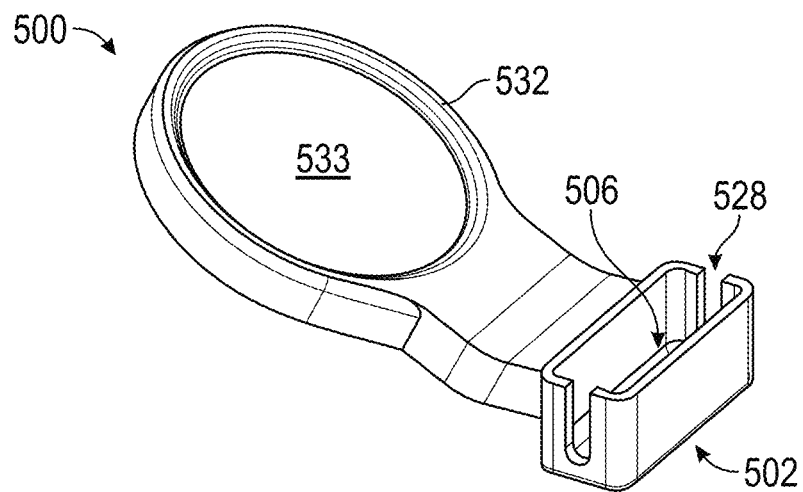
FIGS. 5A-5C schematically illustrate multi-perspective views of another example of a treatment device, which has an open configuration and slots configured for receiving the nerve.
Figure 5B:
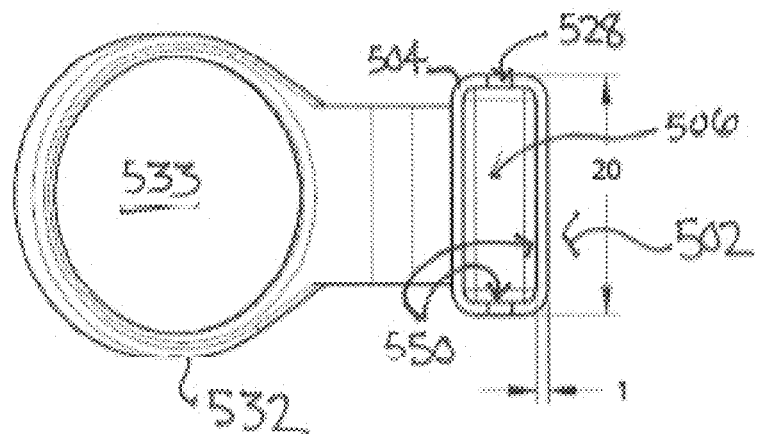
Figure 5C:
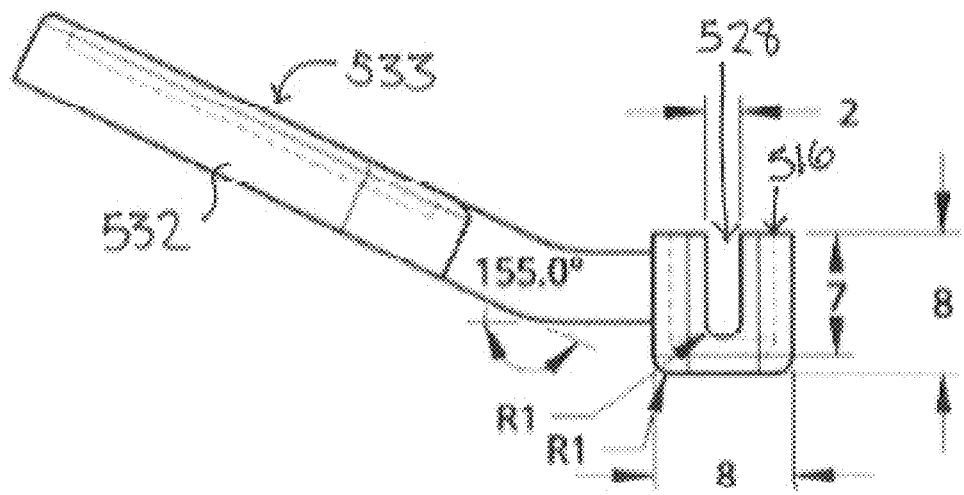

FIGS. 5A-5C schematically illustrate multi-perspective views of another example of a treatment device 500. FIGS. 5A-5C include examples of suitable, but non-limiting dimensions (in mm) for various portions of the treatment device 500. FIG. 5A depicts a perspective view of the treatment device 500. FIG. 5B depicts a top view of the treatment device 500. FIG. 5C depicts a left side view of the treatment device 500. The treatment device 500 may comprise an open bath design similar to the treatment device 100. The treatment device 500 may comprise a generally rectangular body 502. One or more edges and/or corners of the rectangular body 502 may be beveled and/or rounded. The body 502 may comprise left and right endwalls 508, 510 interconnected by a rectangular intermediate body 512. The body 502 may comprise a top surface 516 having an access area 525 that opens into the containment chamber 506. Introduction and/or removal of fluids from the containment chamber 106 (e.g., irrigation and/or aspiration) may be readily accomplished through the access area 525 in devices comprising an open bath configuration. The containment chamber 506 may have a generally rectangular configuration. In some embodiments, one or more of the bottom edges along the floor of the containment chamber 506 (e.g., the front, rear, left, right edges) may comprise beveled and/or rounded surfaces 550 as depicted in FIG. 5C. The left and right endwalls 508, 510 may be generally rectangular in shape. Each endwall 508, 510 may comprise a slot 528 extending downward from top surface 516. The slots 528 may open into the containment chamber 506 and may be configured for receiving and holding the nerve 50. The slots 528 may have a substantially uniform width along the entire height of the slot from the top surface 516 to a bottom of the slot 528 where the nerve 50 is configured to sit. The bottom of the slots 516 may comprise rounded (e.g., semicircular) edges configured for supporting the nerve 50. The width of the slots 528 may be approximately equal to or greater than the diameter of the target nerve 50. The slots 528 may effectively serve the combined functions served by the apertures 126 and slits 128 of the treatment device 100. The body 502 of the treatment device 500 may not comprise any compliant flanges configured to bend in order to receive the nerve 50.

In some embodiments, the bottom of the slots 528 may be positioned a height above the floor, or a bottom point of the floor, of the containment chamber 506. As described elsewhere herein, the treatment device 500 may be configured to receive the isolated segment of the nerve 50 in a slightly bent or curved orientation, such that the nerve droops downward between the slots 528. An anastomosis 52 of the nerve 50 may be positioned generally in the center of the containment chamber 506. As described elsewhere herein, the beveled or rounded surfaces 550 interconnecting the bottom edge of the slots 528 and the floor of the containment chamber 506 may help support the nerve 50 and more evenly distribute the weight of the nerve across the length of the body 502 such that the nerve 50 is not overly stressed at the point where the nerve 50 crosses the inner bottom edge of the slots 528. In some embodiments, the height difference between the bottom of the slots 528 and the bottom of the floor of the containment chamber 506 may be large enough such that the nerve 50 may be fully submerged in a central portion of the containment chamber 506 without the height of the contained solution rising above the bottom of the slot 528. In some embodiments, the height difference between the bottom of the slots 528 and the bottom of the floor of the containment chamber 506 may be large enough such that the nerve 50 may be fully submerged in a central portion of the containment chamber 506 without the height of the contained solution rising above the top of the nerve 50 where it sits in the slot 528 or without the height of the contained solution rising above a lower portion of the nerve 50 where it sits in the slot 528 (e.g., the lower quarter, third, half, two-thirds, or three quarters of the nerve 50). In this manner, the nerve 50 may serve to at least partially fluidly seal a bottom portion of the slots 528 when the nerve 50 sits in the slots 528 and may facilitate retention of the contained solution within the containment chamber 506, depending on the volume added, if the nerve 50 forms a substantially snug fit with the slot 528. For example, the height difference may be at least about 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.0 mm, 6.5 mm, 7.0 mm, 7.5 mm, 8.0 mm, 8.5 mm, 9.0 mm, 9.5 mm, or 10 mm.

The handle 532 of the treatment device 500 may comprise a finger detent 533 on which a user may place a finger (e.g., a thumb) to facilitate the user handling the treatment device 500 with his or her fingers. The finger detent 533 may comprise a generally circular shape. The diameter of the finger detent may be equal to or larger than the length of the body 502 of the treatment device 500 as shown in FIG. 5B. The finger detent 533 may be surrounded by a thin rim. In some embodiments, both upper and lower surfaces of the handle 532 may comprise a finger detent 533. In some embodiments, the finger detent 533 may comprise a same or different material from the remainder of the handle 532. For example, the finger detent 533 may comprise a softer material. In some embodiments, the finger detent 533 may be a void space extending from the top surface to the bottom surface of the handle 532.

In various embodiments, the handles may comprise one or more curves and/or angles. The handle 532 comprises an upward angle as the handle 532 extends distally. The proximal end of the handle 532 may interconnect with the body 502 at or near the top surface 516 of the body 502. The handle 532 may be disposed more toward the top of the body 502 than the bottom of the body 502. The positioning of the handle 532 on the body 502 and/or the upward angle of the handle 532 may advantageously elevate the majority of the handle 532 out of the surgical field of view. In some embodiments, the handle 532 may be disposed more toward the bottom of the body 502. In some embodiments, the handle 532 may be disposed more towards the left side or the right side of the body 502. In some embodiments, the handle 532 may be disposed toward one of the four general corners of the rear side of the body 502. In some embodiments, the handle 532 may be angled downward, to the right, and/or to the left.

Figure 6A:
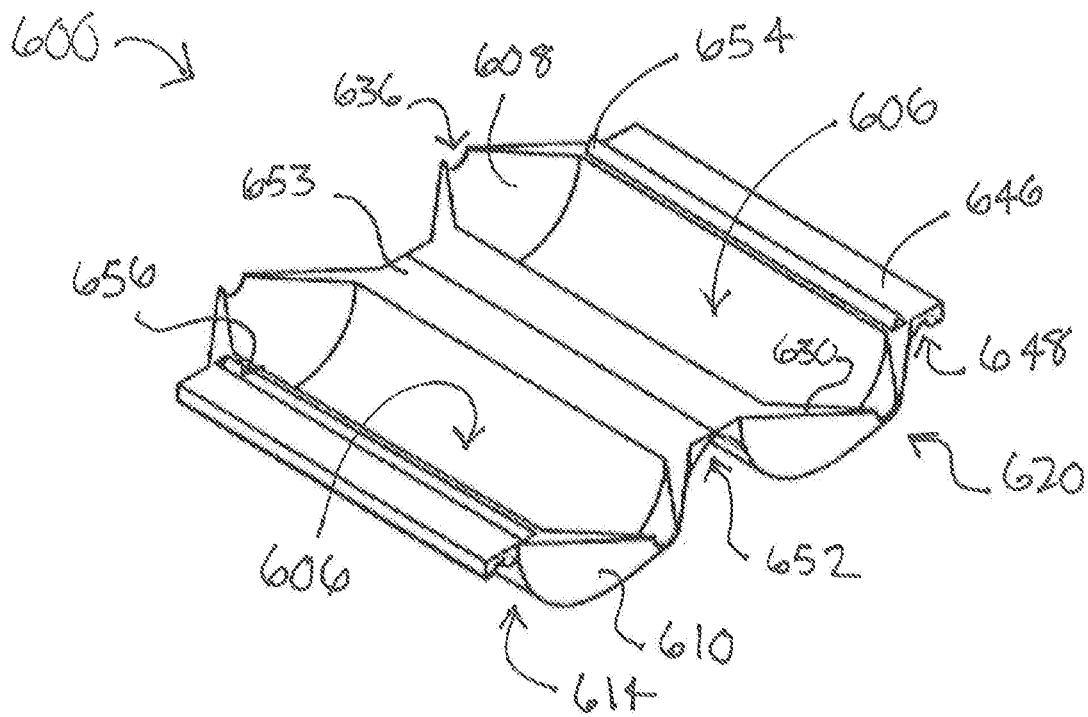
FIGS. 6A-6G schematically illustrate multi-perspective views of another example of a treatment device, which comprises hinged upper and lower bodies shown in an opened configuration.
Figure 6B:
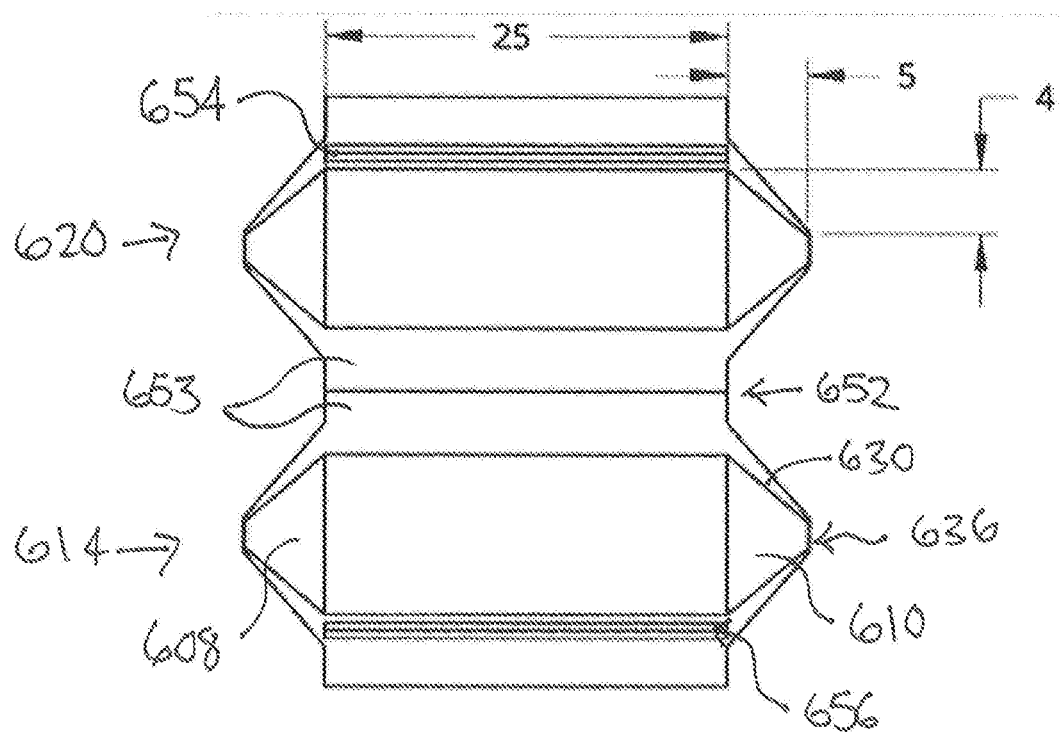
Figure 6C:
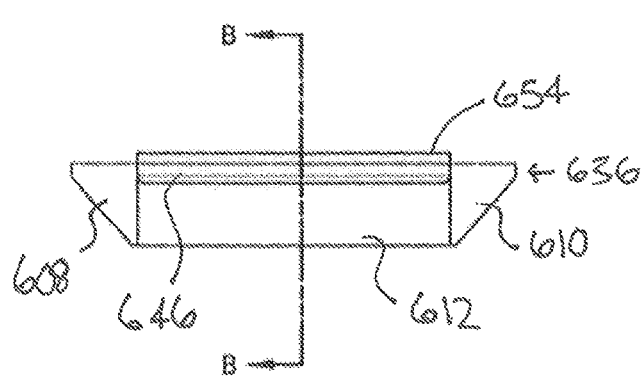
Figure 6F:
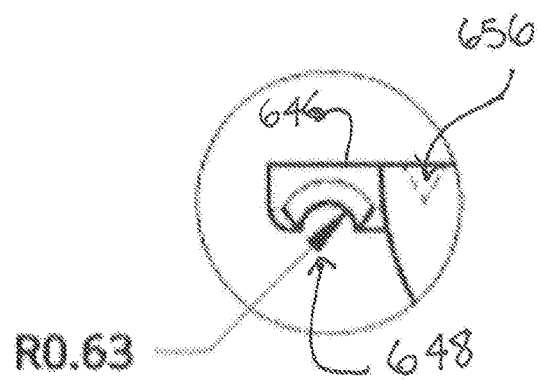
Figure 6D:
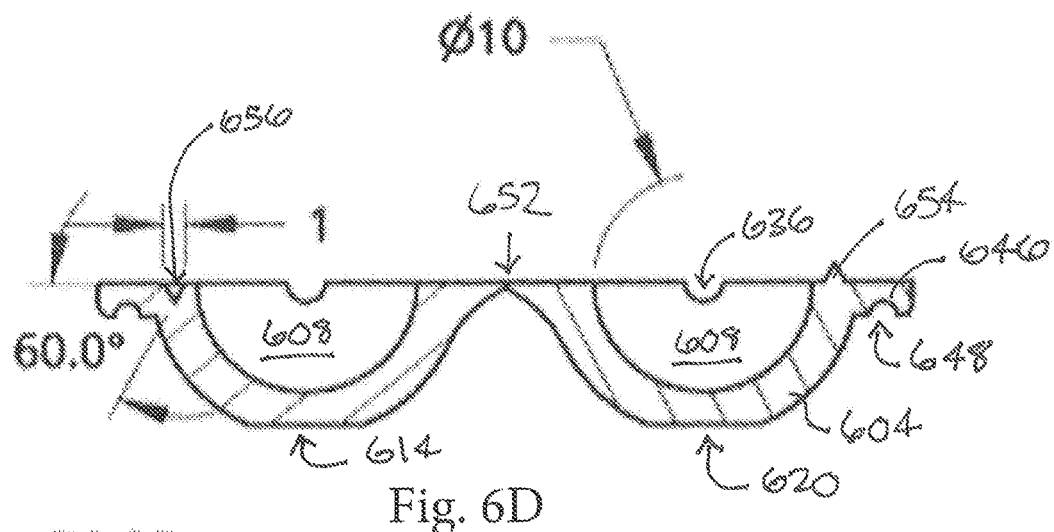
Figure 6E:
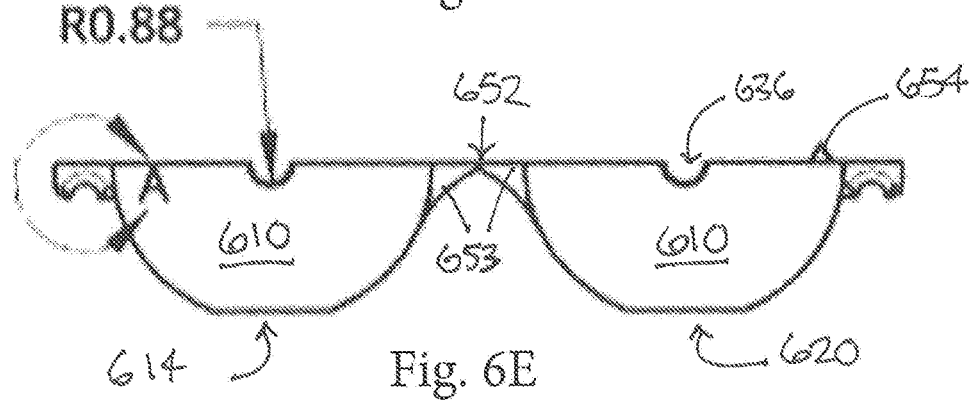
Figure 6G:
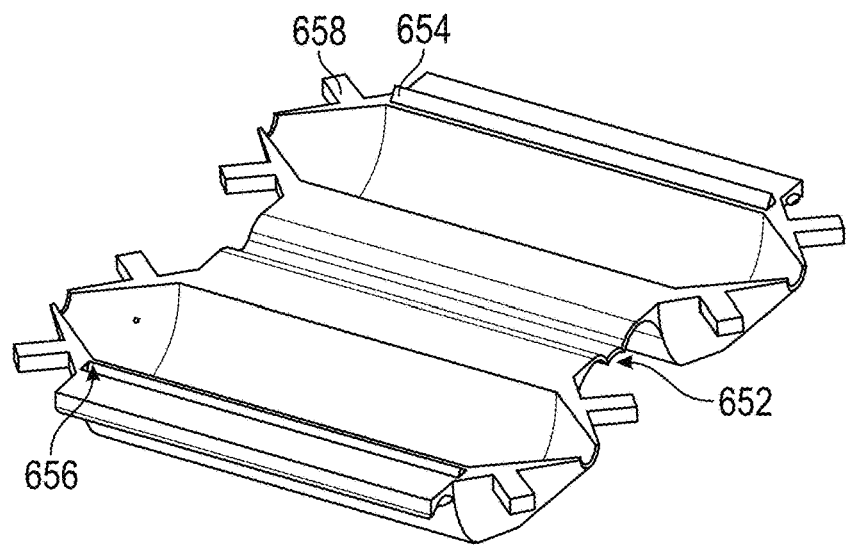

FIGS. 6A-6G schematically illustrate multi-perspective views of another example of a treatment device 600 in an opened configuration configured for receiving the nerve 50. FIGS. 6A-6G include examples of suitable, but non-limiting dimensions (in mm) for various portions of the treatment device 600. FIG. 6A depicts a perspective view of the treatment device 600. FIG. 6B depicts a top view of the treatment device 600. FIG. 6C depicts a front view of the treatment device 600. FIG. 6D depicts a cross-sectional view of the section B-B indicated in FIG. 6C. FIG. 6E depicts a right side view of the treatment device 600. FIG. 6F depicts a close-up view of the inset A indicated in FIG. 6E. FIG. 6G depicts a perspective view of a variation of the treatment device 600 illustrated in FIG. 6A. The treatment device 600 may comprise many similar or identical features to the treatment device 300. The treatment device 600 may comprise a lower body 614 and an upper body 620 configured to be positioned in an open configuration configured to receive the nerve 50 into a containment chamber 606 and in a closed configuration (not shown) in which the isolated segment of the nerve 50 is entirely circumferentially enclosed by the body 602 of the treatment device 600. The body 602 may comprise a split 629 between the lower body 614 and the upper body 620 in the closed configuration. The body 602 may comprise lips 646, which may comprise grooves 648 as described elsewhere herein. The grooves 348 may be configured to retain a securing device which is configured to secure the body 602 in a closed configuration. The body 602 of the treatment device 600 may be generally cylindrical in shape. The body 602 may comprise a partially flattened lower outer surface and/or a partially flattened upper outer surface, as shown in FIGS. 6D and 6E, which may facilitate resting the device 600 stably on a flat surface. The containment chamber 606 may be generally cylindrical in shape, at least along the length of the intermediate body 612.

The lower body 614 and the upper body 620 may be joined together at a hinge 652. The hinge 652 may be positioned circumferentially opposite the lips 646 in the closed configuration. The hinge 652 may form or may be part of a flange 653 that extends laterally from the intermediate body 612 along at least a partial length of the intermediate body 612. The flange 653 may be used similar to a handle in the closed configuration to facilitate handling the treatment device 600. The flange may join the lower body 614 to the upper body 620. Unlike the example depicted in FIGS. 3A-3E, in which the deformation or strain experienced by the body 302 in biasing apart the upper and lower bodies 314, 320 may generally be distributed circumferentially around the body 302, the body 602 may be configured to isolate the deformation to the hinge 652. The hinge 652 may be a living hinge as illustrated in FIGS. 6A-6F. The living hinge 652 may be a thinned out portion of the body 602 which is inherently more flexible than the rest of the body 602 due to its reduced dimensions, even if the hinge 652 comprises the same material as the rest of the body 602. In other embodiments, the hinge 652 may be a mechanical hinge comprising separable articulating components.

The body 602 may comprise a ridge 654 extending from the bottom surface 622 of the upper body 620 along at least a portion of the length of the intermediate body 612 and a corresponding trench 656 extending from the top surface 616 of the lower body 614 along the same length of the intermediate body 612 as the ridge 654. The ridge 654 may be configured to mate with the trench 656 in an interference fit. The interference fit may help fluidly seal the containment chamber 606 in a closed configuration and/or may help secure the lower body 614 to the upper body 620. In some embodiments, the ridge 654 may be disposed on the lower body 614 and the trench 656 may be disposed on the upper body 620. The ridge 654 and trench 656 may be disposed on the intermediate body 612, on the lips 346, or between the intermediate body 612 and lips 346 (e.g., having portions disposed in both). In some embodiments, the body 602 may comprise multiple mating interference features (e.g., two or more rows of ridges 654 and trenches 656).

The body 602 of the treatment device may comprise non-flat left and right endwalls 608, 610. In some embodiments, the endwalls 608, 610 may comprise generally conical shapes, in a closed configuration, as shown in FIG. 6A-6C. The endwalls 608, 610 may be generally frustoconical in shape, in a closed configuration, with generally circular apertures 626 forming apexes of the conical structures. The split 629 between the lower body 614 and the upper body 620 may divide the frustoconical endwalls 608, 610 evenly in half. The inner surface of the frustoconical endwalls 608, 610 may function as beveled surfaces 650 similar to beveled surfaces described elsewhere herein which facilitate supporting the isolated segment of the nerve 50 across a transition from the aperture 526 to the lower floor of the containment chamber 606. In some embodiments, a frustoconial endwall 608, 610 may comprise a length extending from the intermediate body 612 to the aperture 626 that is at least about 1 mm, 2 mm, 3 mm, 4 mm, 5 mm, 6 mm, 7 mm, 8 mm, 9 mm, or 10 mm in length. As shown in FIGS. 6A and 6B, the frustoconical endwalls 608, 610 may decrease or taper in thickness as the endwalls 608, 610 extend away from the intermediate body 612. The endwalls may be generally compliant and may function similar to flanges 130 described elsewhere herein. The endwalls 608, 610 may be more compliant toward and near the apertures 626 than near the intermediate body 612. The endwalls 608, 610 may be somewhat deformable such that the circumferences of the apertures may be effectively expandable to accommodate nerves 50 of different diameters. The frustoconical configuration which extends the flange-like structures at least partially in a longitudinal (as opposed to radial) direction may facilitate a circumferential bending of the endwall flanges 608, 610 which allows accommodation of nerves 50 having diameters larger than the unbiased diameter of the apertures 626. Similarly, the configuration may promote formation of a compressive seal circumferentially around the nerve 50 within the apertures 626.

As shown in the variation depicted in FIG. 6G, the treatment device 600 may comprise one or more manipulation tabs 658 extending from the body 602 (e.g., extending laterally). The manipulation tabs 658 may allow the user to handle and/or manipulate the treatment device 600 (e.g. move the lower body 614 and/or upper body 620 between closed and open positions). The manipulation tabs 658 may be generally rectangular in shape. The manipulation tabs 658 may be no more than approximately, 1 mm, 2 mm, 3 mm, 4 mm, 5 mm, 6 mm, 7 mm, 8 mm, 9 mm, or 10 mm in length. In some embodiments the manipulation tabs 658 may extend laterally from the endwalls 608, 610. For example, as shown in FIG. 6G four manipulation tabs 658 may extend from the body 602. Two manipulation tabs 658 may extend from the front portion of the body 602 and two manipulation tabs 658 may extend from the rear portion of the body 602. Two manipulation tabs 658 may extend from the left endwall 608 and two manipulation tabs 658 may extend from the right endwall 610. The manipulation tabs 658 may extend in directions that are offset by approximately 90 degrees from each other.

Figure 7:
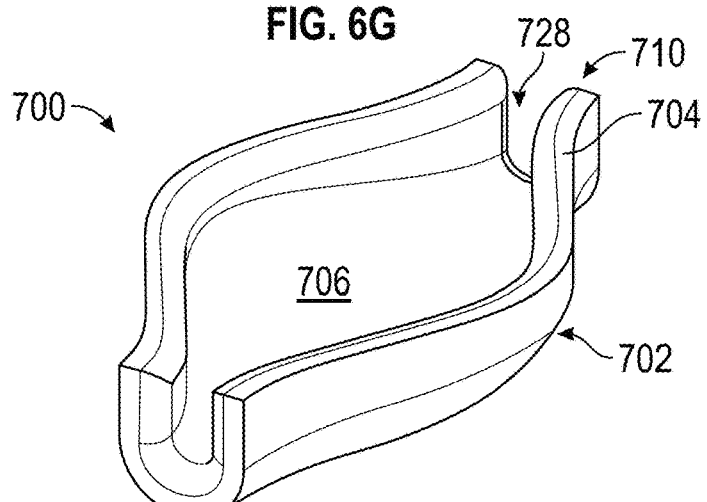
FIG. 7 depicts a perspective view of another example of a treatment device, which comprises an open configuration and a curved body having variable width and open slots configured for receiving the nerve.

FIG. 7 depicts a perspective view of another example of a treatment device 700. The treatment device 700 comprises an open bath configuration as described elsewhere herein. The treatment device 700 may comprise a non-uniform width across the length of the body 702. The containment chamber 706 may comprise a non-uniform width across the length of the body 702. In some embodiments, the width profile of the body 702 may mirror the width profile of the containment chamber 706. In some embodiments, the height profile of the body 702 may mirror the depth profile of the containment chamber 706. The width may be smallest at left and right ends of the body 702 and greatest at a central portion of the length (e.g., at the center). The body 702 may be symmetric about a midline dividing the left and right sides of the treatment device 700. In some implementations the left and/or right ends of the body 702 may comprise sufficiently narrow widths such that they facilitate handling (e.g., grasping by the user's fingers or tools). The body 702 may be symmetric about a midline dividing front and rear sides of the treatment device 700. The body 702 may comprise a generally curved front surface and a generally curved rear surface. The body 702 may comprise a generally round bottom. The treatment device 700 may comprise a containment chamber 702 comprising a generally non-flat floor. The floor of the containment chamber 702 may comprise a continuously smooth surface. The floor of the containment chamber 702 may be deepest at a central point of the containment chamber 702, which may be configured for receiving an anastomosis 52. The floor may increase in depth from the left and right sides of the treatment device 700 toward the center. The continuously smooth floor may serve the same function as the beveled surfaces 550 described elsewhere herein as it drops from the left and right sides toward the center. The floor may increase in depth from the front and rear sides of the treatment device 700 toward the center. The left and right endwalls 708, 710 may comprise only the thickness of the left and right edges of the sidewall 704 forming the intermediate body 712 that extends from the left end to the right end of the body 702. The sidewall 704 may be shaped at the left and right endwalls 708, 710 to define slots 728, similar to slots 528 described elsewhere herein, configured for receiving the nerve 50. The treatment device 700 may be configured to receive a nerve 50 such that the nerve 50 at least partially seals the slots 528 when seated in the slots 528, as described elsewhere herein. The floor may reach height at the front center of the containment chamber 706 and/or at the rear center of the containment chamber 706 that is lower than, approximately the same as, or higher than the height reached adjacent the slots 728. The floor of the containment chamber 706 may be designed to substantially isolate a volume of the contained solution near the central portion of the treatment device 700, such as around an anastomosis 52 of a nerve 50.

Figure 8A:
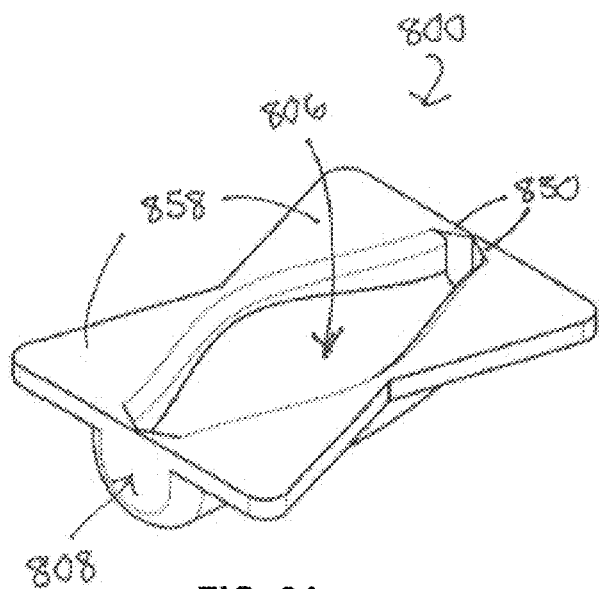
FIGS. 8A-8E schematically illustrate multi-perspective views of another example of a treatment device, which comprises an open configuration and slits in the opposing endwalls configured for receiving and retaining the nerve.
Figure 8B:
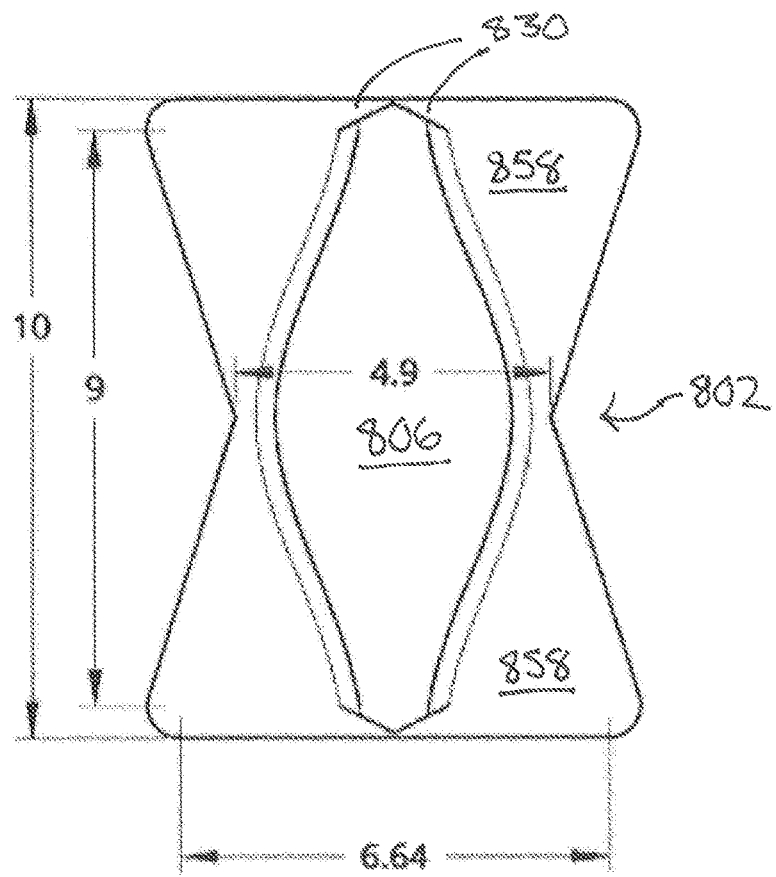
Figure 8C:
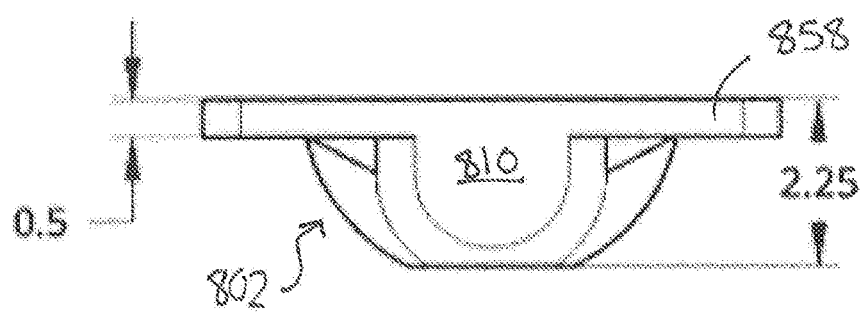
Figure 8D:
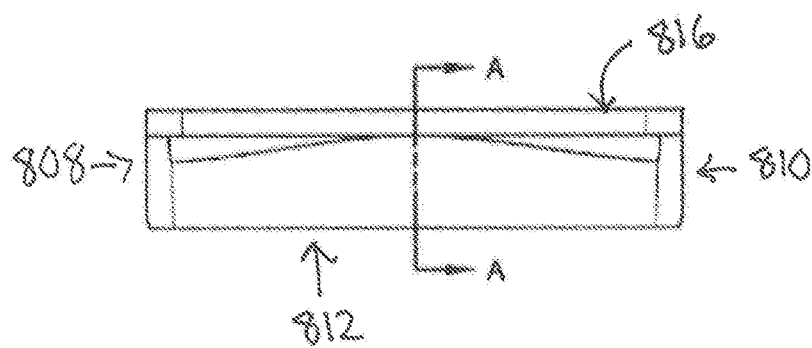
Figure 8E:
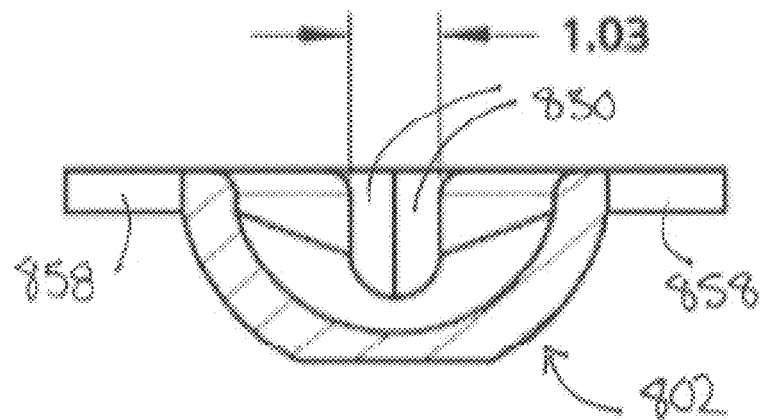

FIGS. 8A-8E schematically illustrate multi-perspective views of another example of a treatment device 800. FIGS. 8A-8E include examples of suitable, but non-limiting dimensions (in mm) for various portions of the treatment device 800. FIG. 8A depicts a perspective view of the treatment device 800. FIG. 8B depicts a top view of the treatment device 800. FIG. 8C depicts a left or right side view of the treatment device 800. FIG. 8D depicts a front or rear view of the treatment device 800. FIG. 8E depicts a cross-sectional view of the section A-A indicated in FIG. 8D. The body 802 of the treatment device may comprise a configuration the same or similar in shape to body 702 described with respect to FIG. 7. Treatment device 800 may comprise left and right endwalls 808, 810 which extend inwardly in a generally radial direction from the left and right edges of the intermediate body 812 to form left and right surfaces of the containment chamber 806. The left and right endwalls 808, 810 may comprise slits 828 similar to slits 128 described elsewhere herein. The slits 828 may extend from an upper surface 816 of the body 808. The slits 828 may extend in a substantially vertical direction. The slits may extend all the way to the bottom edge of the left and right endwalls 808, 810 as seen in FIG. 8E. The slits 828 may divide the endwalls 808, 810 into one or two flanges 830. The flanges 830 may be the same or similar to the flanges 130 described elsewhere herein. The distal edges of the flanges 830 may form opposing edges of the slits 828. Unlike the treatment device 100, the endwalls 808, 810 may not comprise any apertures. The treatment device 800 may be configured to receive and to hold or retain the nerve 50 between opposing edges of the flanges 830, which may be biased inward and/or outward to accommodate the diameter of the nerve 50, as described elsewhere herein. In some embodiments, the slit comprises only a single vertical separation within the sidewall 804 dividing a flange 830 from another flange 830 or a flange 830 from a less compliant portion of the sidewall 804. In some embodiments, the separation forming the slit 828 may extend in an at least somewhat horizontal direction near the bottom of the one or two flanges 830 such that the slit 828 extends below at least a portion of the one or two flanges 830 allowing greater flexibility of the flange 830. In the case of two flanges 830, the split may diverge in opposite directions to extend beneath both flanges 830. For instance, the slits 829 may extend at least partially along the left and/or right semicircular intersection of the endwalls 808, 810 with the floor of the containment chamber 806 illustrated in FIG. 8E.

The treatment device 800 may comprise one or more manipulation tabs 858, which may comprise similar features to manipulation tabs 658 described elsewhere herein. The manipulation tabs 858 may comprise generally thin flat surfaces extending laterally from the body 802 of the treatment device 800. The flat surfaces of the manipulation tabs 858 may comprise larger surface areas which facilitate grasping by a user's fingers or by surgical tools. In some embodiments, the manipulation tabs 858 may comprise generally triangular shapes having substantially uniform thickness between upper and lower surfaces, as illustrated in FIGS. 8A-8E. The manipulation tabs 858 may be coplanar with other portions of a top surface 816 of the body 802. The left and right edges of the manipulation tabs may extend no further longitudinally than the left and right endwalls 808, 810 of the device. The treatment device 800 may comprise four manipulation tabs 858 as seen in FIGS. 8A-8E. The manipulation tabs 858 may generally be positioned at front-left, front-right, rear-left, and rear-right corners of the body 802.

Figure 9:
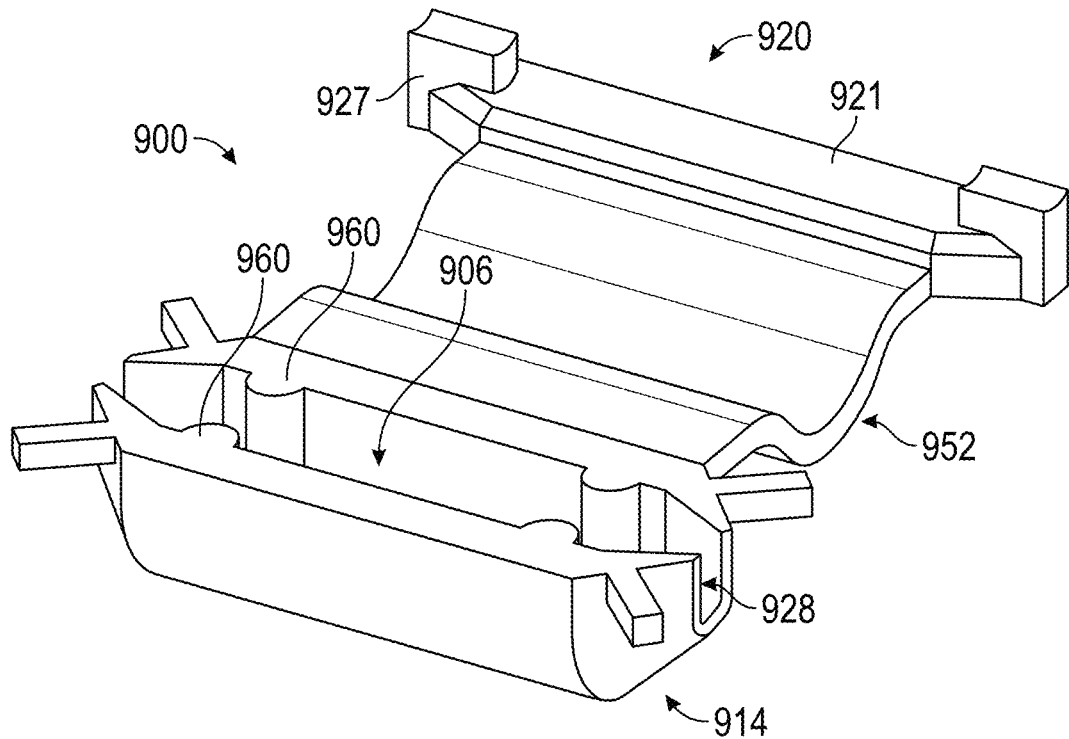
FIG. 9 illustrates a perspective view of another example of a treatment device. The treatment device comprises an upper body hinged to the lower body and configured to be inserted into the containment chamber to fluidly seal the chamber.

FIG. 9 illustrates a perspective view of another example of a treatment device 900. Treatment device 900 may comprise a lower body 914 comprising features generally similar to the lower body 614 of treatment device 600. As seen in FIG. 9, the left and right endwalls 908, 910 may each comprise the bottom half of a frustoconical shell which continues to extend vertically upward in a linear manner for some height. The left and right endwalls may define slots 928 similar to slots 528 described elsewhere herein. The configuration of the endwalls 908, 910 may be configured to exert a compressive force against a nerve 50 received in the slots 528 and to form a compressive seal with the nerve 50, as described elsewhere herein.

The body 902 of the treatment device 900 may comprise an upper body 920 which is joined to the lower body 914 by a hinge 952 (e.g., a living hinge), as described elsewhere herein. The upper body 920, or at least a portion thereof, may be configured to be at least partially received within the containment chamber 906 to fluidly seal an access area 924 formed in a top surface 916 of the lower body 914 and/or to fluidly seal at least a portion (e.g., an upper portion) of the slots 928 when the treatment device 900 is placed in a closed configuration. As shown in FIG. 9, the inserted portion 921 of the upper body 920 may comprise a shape or an outer periphery configured to generally mate with an inner periphery of the containment chamber 906. The upper body 920 may or may not comprise a portion, other than the hinge 952, which extends over or covers the top surface 916 of the lower body 914 outside of the access area 924 of the containment chamber 906. The inserted portion 921 configured to be received in the containment chamber 906 may comprise left and/or right vertical extensions 927 configured to at least partially fill the left and/or right slots 928. The left and right vertical extensions 927 may be configured to extend longitudinally outward beyond the left and right endwalls 908, 910, respectively. The left and right vertical extensions 927 may be configured to extend longitudinally inward beyond the left and right slots 928, respectively. The vertical extensions 927 may be configured to extend below a bottom of the remaining portions of the inserted portion 921 in a closed position, such that inner surfaces of the vertical extensions 927 may at least partially form left and right inner surfaces of the containment chamber 1106. The bottom of the vertical extensions 927 may comprise concave surfaces configured to be pressed into contact with a generally round nerve 50 to form a fluid seal around the top of the nerve 50 within the slot 928. The concave surfaces may be generally semicircular (e.g., the top half or less of a circle) to conform to a nerve 50 having a generally circular cross-section. In some embodiments, the vertical extensions 927 may comprise the same material as the rest of the upper body 920 and/or as the lower body 914. In some embodiments, the vertical extensions 927 may comprise a different (e.g., a softer or more compliant) material than the rest of the upper body 920 and/or the lower body 914.

The lower body 914 of the treatment device 900 may comprise one or more support ribs 960 disposed within the containment chamber 906. The support ribs 960 may extend in a generally vertical direction, and may extend from a top surface 916 of the lower body 914 to a floor of the containment chamber 906. The support ribs 960 may have a generally round (e.g., semicircular) cross-sectional shape. The support ribs 960 may comprise the same material as the rest of the lower body 914 or a different (e.g., softer material). The support ribs may provide structural support to the containment chamber 906 such as by increasing the rigidity of the containment chamber 906, particularly in the transverse direction. The support ribs 960 may be configured to frictionally engage the isolated segment of the nerve 50 extending between the left and right slots 928. The support ribs 960 may facilitate elevating or suspending the nerve 50 off of the floor of the containment chamber 906 which may advantageously allow for more thorough fluid encapsulation of the nerve 50, particularly around a central portion (e.g., where an anastomosis may be positioned). In some implementations, the nerve 50 may be positioned between front and rear opposing support ribs 960. The nerve 50 may be disposed between the support ribs 960 at an appropriate height by biasing the support ribs 960 apart (e.g., by biasing a front portion of the lower body 914 away from a rear portion, as separated by the slots 928) and allowing the nerve 50 to slide or fall under gravity into the proper position before relaxing the force separating the support ribs 960. The support ribs 960 may be biased apart via the user's fingers and/or using appropriate surgical tools as described elsewhere herein.

Figure 10:
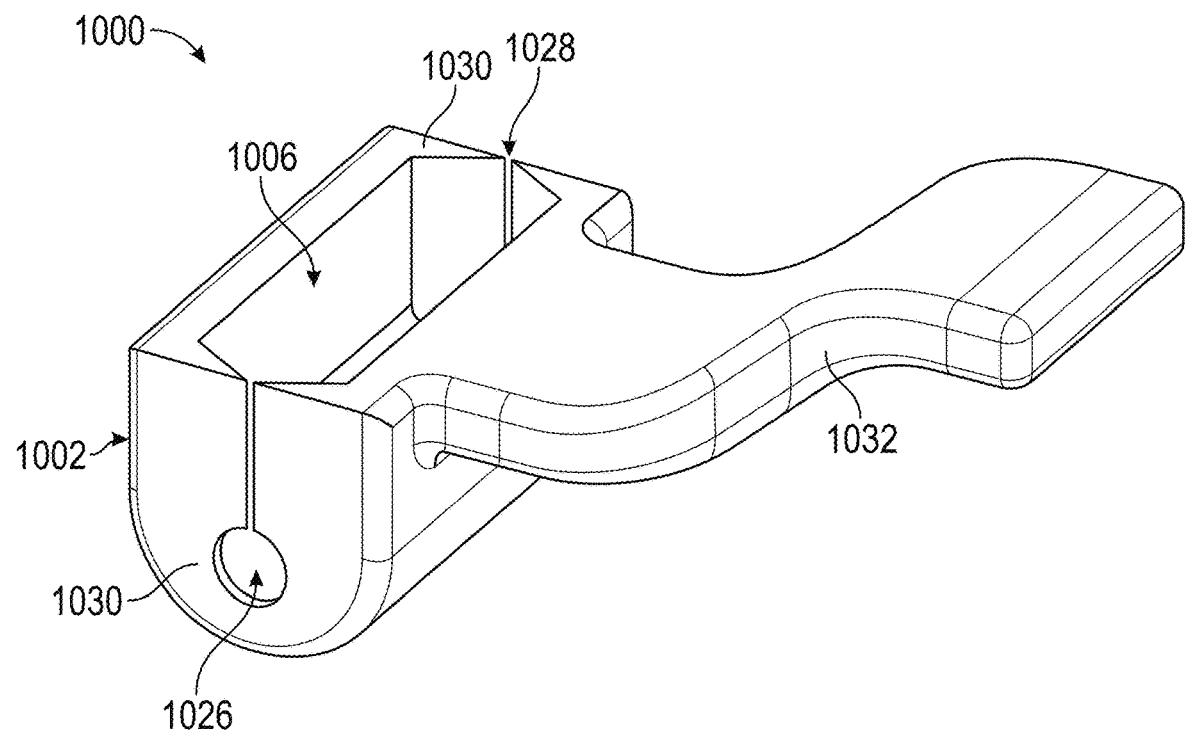
FIG. 10 illustrates a perspective view of another example of a treatment device. The treatment device is similar to the treatment device illustrated in FIG. 1 but comprises a ladle-type handle.

FIG. 10 illustrates a perspective view of another example of a treatment device 1000. Treatment device 1000 may comprise similar features to treatment device 100. The handle 1032 may comprise a ladle-type configuration. The handle 1032 may comprise a curve in an upward direction. The curve may be gradually spaced out over at least a majority of the length of the handle 1032. The curve may comprise an inflection point at which the direction of the curvature changes, as shown in FIG. 10. The distal end of the handle may be positioned above the top surface 1016 of the body 1002 of the treatment device 1000. The distal end of the handle 1032 may be oriented in a substantially horizontal direction.

Figure 11A:
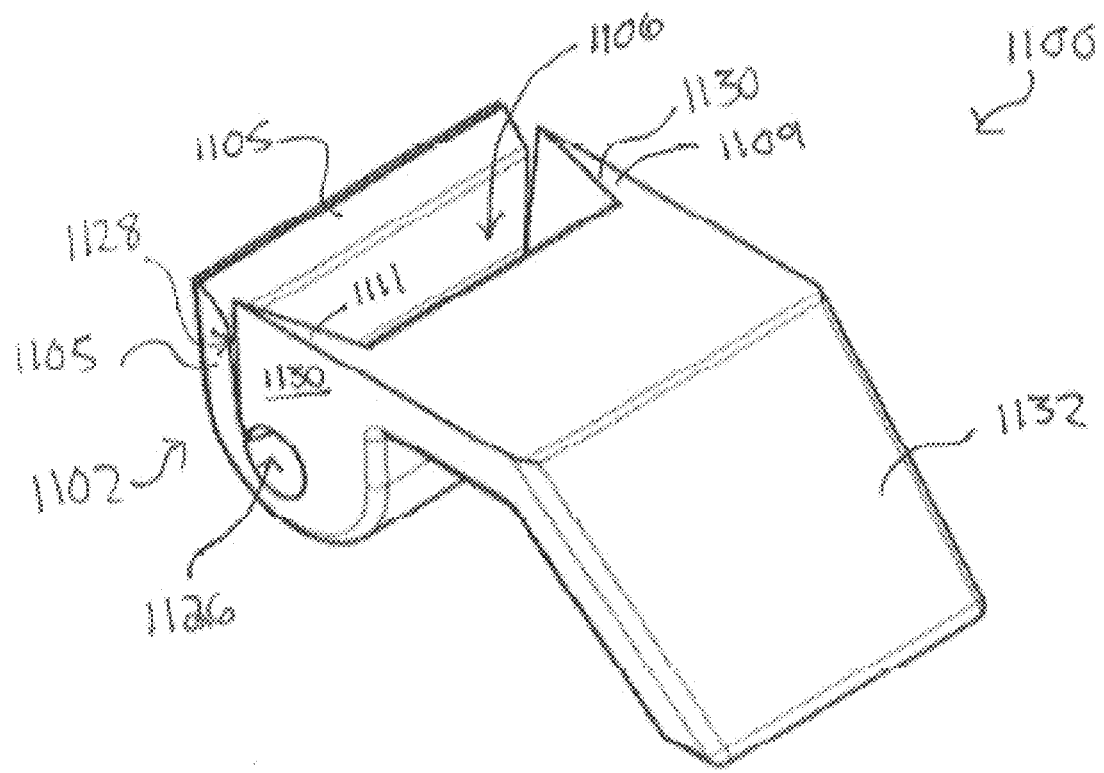
FIGS. 11A-11E schematically illustrate multi-perspective views of another example of a treatment device similar to the treatment device illustrated in FIG. 1. The treatment device has opposing slits which are positioned along an intersection with a front wall to created flanged endwalls.
Figure 11B:
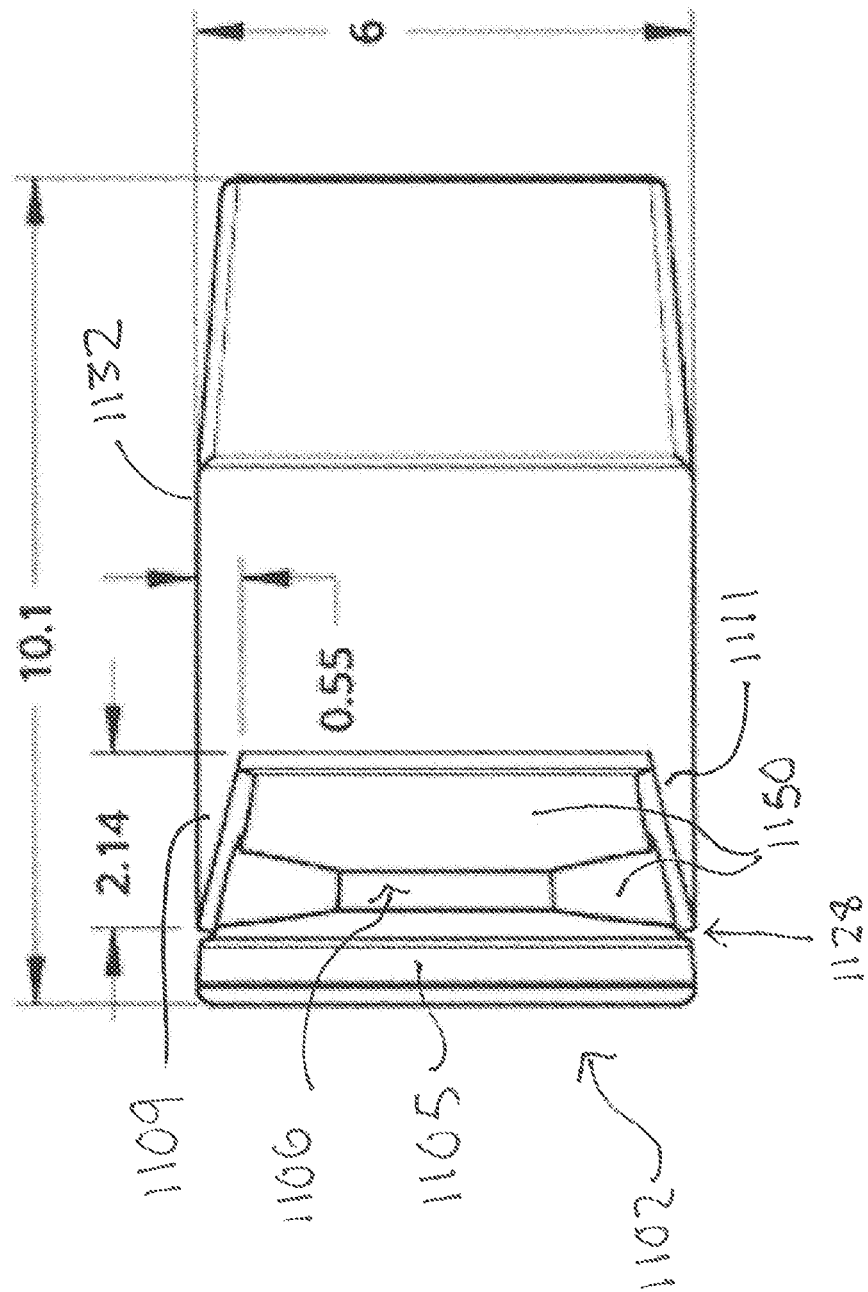
Figure 11C:
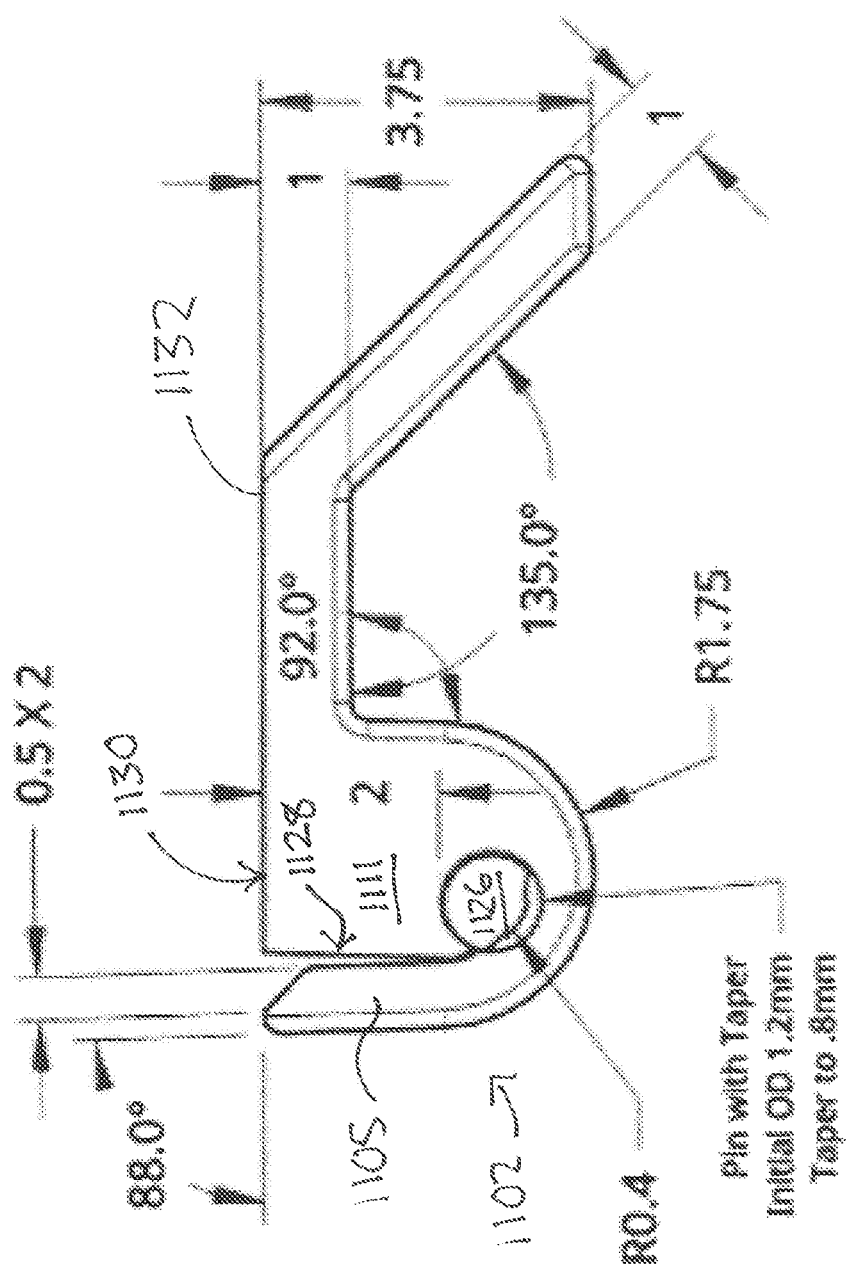
Figure 11D:
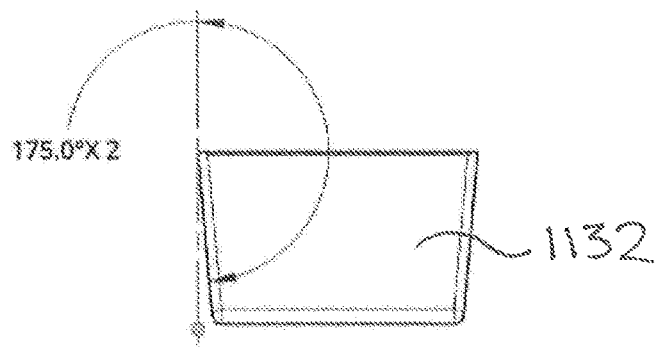
Figure 11E:
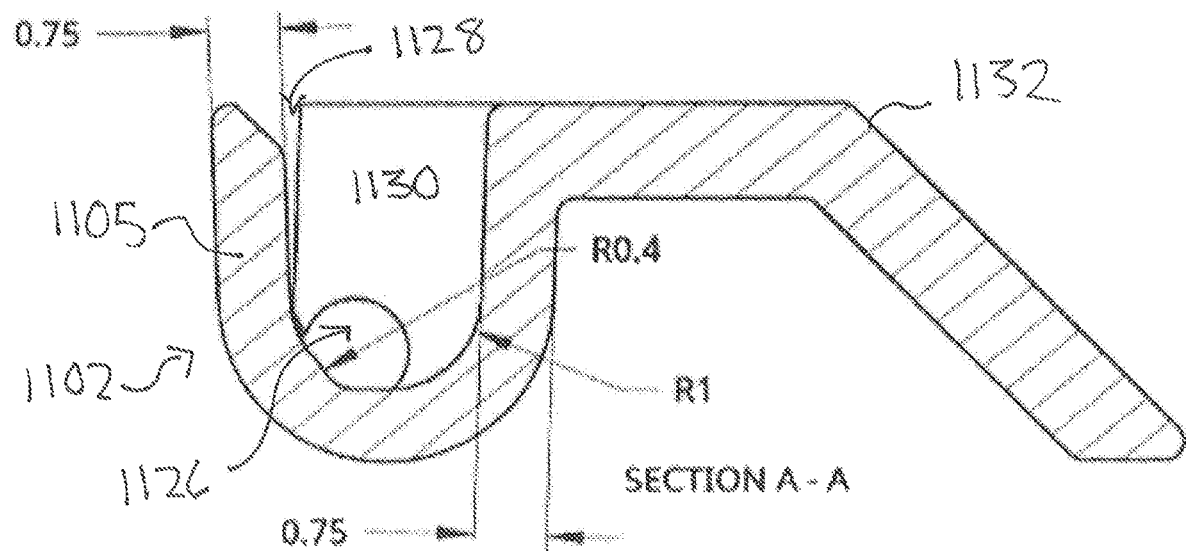

FIGS. 11A-11E schematically illustrate multi-perspective views of another example of a treatment device 1100. FIGS. 11A-11E include examples of suitable, but non-limiting dimensions (in mm) for various portions of the treatment device 1100. FIG. 11A depicts a perspective view of the treatment device 1100. FIG. 11B depicts a top view of the treatment device 1100. FIG. 11C depicts a right side view of the treatment device 1100. FIG. 11D depicts a rear view looking down on a portion of the handle 1132 of the treatment device 1100. FIG. 11E depicts a cross-sectional view of a section taken along a midline between left and right sides of the treatment device 1100 transverse to the longitudinal axis. The treatment device 1100 may comprise features similar to treatment device 100 and/or treatment device 1000. The slits 1128 may be disposed along the right and left endwalls 1108, 1110 along an intersection between a front portion 1105 of the sidewall 1104 forming a front inner surface of containment chamber 1106 and the left and right portions 1109, 1111 of the sidewall 1104 forming the left and right inner surfaces of the containment chamber 1106. The slits 1128 may define a single flange 1130 on each endwall 1108, 1110. The flanges 1130 may form the majority of the surface area of the endwalls 1108, 1110 and may form the entire inner surface of the containment chamber 1106. The distal edges of the flanges 1130 may oppose the front sidewall 1105 that forms the intermediate body 1112 along the front surface of the treatment device 1100. The distal edges of the flanges 1130, in an unbiased configuration, may be positioned in close proximity to the front sidewall 1105, may be positioned in contact with the front sidewall 1105, or may partially overlap the left and right edges of the front sidewall 1105, similar to the distal edges of flanges 130 described elsewhere herein. The positioning of the slits 1128 as described which more definitively proportions the sidewall 1104 between a front sidewall 1105 and left and right sidewalls 1109, 1111 may make the front sidewall 1105 relatively more compliant. The front sidewall 1105 may be readily bendable in a forward direction away from the distal end of the flanges 1130, which may advantageously facilitate insertion of the nerve 50 through the slits 1128 to be received in apertures 1136. The top edge of the front sidewall 1105 may be angled or beveled downward in the direction of the containment chamber 1106, which may advantageously help guide the nerve 50 into the slits 1128 during introduction of the nerve 50 into the treatment device 1100.

The apertures 1136 of treatment device 1100 may be disposed off-center in the direction transverse to the longitudinal axis on the endwalls 1108, 1110. For instance, the apertures 1136 may be disposed along the intersection of the front sidewall 1105 and the left and right sidewalls 1109, 1111. The slits 1128 may interest the circumferences of the apertures 1126 along the frontward most points of the circumferences as shown in FIGS. 11A and 11C. The front wall 1105 may merge with the left and right sidewalls 1109, 1111 generally along a bottom and/or rear portion of the circumference of the apertures 1126. The positioning of an entire aperture 1136 underneath a single flange 1130 may advantageously make the flange 1130 more flexible as a longer horizontal length of the flange 1130 may be separable from the remainder of the endwall 1108, 1110.

As shown in FIG. 11C, the containment chamber 1106 may comprise beveled surfaces 1150, as described elsewhere herein, interconnecting front, rear, left, and/or right inner surfaces of the containment chamber 1106 to a floor of the containment chamber 1106. The positioning of the slits 1128 and the apertures 1126 more toward the front wall 1105 may shift the floor of the containment chamber 1106 more toward the front of the body 1102 of the treatment device 1100.

The treatment device 1100 may comprise a handle 1132 having a downward angle as shown in FIG. 11C. The handle 1132 may extend laterally from the body 1102 of the treatment device 1100 (e.g., from the top of the treatment device 1100) and then bend toward a downward direction. The distal end of the handle 1132 may extend to a vertical position above the bottom of the body 1102, approximately at the same level as the bottom of the body 1102 (as shown in FIG. 11C), or below the bottom of the body 1102.

In various embodiments, the treatment device may be configured to facilitate measuring an action potential (e.g., a compound action potential) and/or to apply an electric stimulus across the isolated segment of the nerve 50. In some embodiments, electrodes may be configured to receive electrodes and to position the electrodes in contact with the nerve. For example, in some implementations, needle-like electrodes may be received through the fluid ports 340 of the treatment device 300. Electrodes may be positioned at left and right ends of the nerve 50 on opposite sides of the anastomosis 52. In other embodiments, the treatment device may comprise specific access ports or windows configured to receive and/or to secure electrodes to the device. In some embodiments, electrodes may be built into the device. For instance, electrodes may be disposed within an inner surface of the containment chamber and configured to be placed into contact with the nerve 50 (e.g., at a left and/or right side of the device). In some embodiments, there may be an electrode configured to serve as a positive terminal and an electrode configured to serve as a negative terminal. In some embodiments, the device may include a ground terminal and/or the negative terminal may be grounded. In some embodiments, the electrodes may be embedded in the polymeric device. The electrodes may be connected via electrical conductors to electrical contacts disposed on an external surface of the device. The body of the treatment device may be fabricated from generally non-conductive materials.

In some implementations, the treatment device may be used for clinical and/or academic research purposes. The treatment device may serve only to isolate a nerve for in situ studies or experiments, such as pharmacological studies and/or electrophysiological studies. In some implementations, the treatment device may be used to perform cell fusion according to protocols other than those described elsewhere herein. For example, in some implementations, the device may be used with fusogens other than PEG. In some implementations, the treatment device may be used during an electrofusion (e-fusion) protocol, in which electrical shocks are applied to the nerve to stimulate cell fusion (similar to an electroporation protocol). The electrodes described elsewhere herein may be useful for performing an electrofusion protocol. In some methods, the nerve treatment device may be used to retain and stably hold the severed ends of a nerve in a juxtaposed position during the physical reattachment (e.g., suturing) of the severed nerve ends.

Solutions

In various embodiments, the solutions applied to the nerve may comprise USP-grade agents in common use. The solutions may contain no new chemical entities and/or non-USP components. When applied in the appropriate sequence, the agents in the solutions are responsible for the primary mechanism of action (PMOA) of the components and method disclosed herein. In some embodiments, exposure to any or all of the solutions described herein during the treatment procedure may be no more than approximately 1, 2, 3, 4, or 5 min each. In preferred embodiments, the exposure may be no longer than 2 minutes.

In some embodiments, the components of the kit may comprise three solutions and a treatment device described elsewhere herein. A priming solution (Solution 1) may comprise methylene blue, which may be the active agent. The priming solution may be hypotonic. The priming solution may be calcium-free (e.g., free of divalent calcium cations, $Ca^{2+}$). The presence of calcium may interfere with cellular biochemical processes and/or may induce massive cellular aggregation and potentially premature fusion). The priming solution may comprise saline. The priming solution may be sterile. The priming solution may be non-pyrogenic. In some embodiments, the priming solution may comprise methylene blue. Without being limited by theory, methylene blue may function as an antioxidant providing protective benefits to the cells, may inhibit or delay Wallerian degeneration of the injured axons, and/or may prevent sealing of the damaged cell membranes.

In some embodiments, a 100 mL volume of the priming solution may contain approximately: 526 mg of Sodium Chloride, USP (NaCl); 502 mg of Sodium Gluconate USP, ($C_6H_{11}NaO_7$); 368 mg of Sodium Acetate Trihydrate, USP ($C_2H_3NaO_2.3H_2O$); 37 mg of Potassium Chloride, USP (KCl); 30 mg of Magnesium Chloride, USP ($MgCl_2.6H_2O$); and 1 mg of Methylene Blue, USP ($C_{16}H_{18}ClN_3S$). The priming solution may made in ddi-$H_2O$ at a pH of approximately 7.4. In some embodiments, the pH may be between approximately 6.5 and 8.0. In some implementations, the priming solution may be or may comprise Plasma-Lyte™ (Baxter International Inc., Deerfield, Ill.).

A fusion solution (Solution 2) may comprise polyethylene glycol (PEG). The PEG may be low molecular weight PEG. In some embodiments, the PEG may comprise a molecular weight (e.g., a number average or weight average molecular weight for a polydisperse sample) no greater than 1,000 Da, 1,500 Da, 2,000 Da, 2,500 Da, 3,000 Da, 3,500 Da, 4,000 Da, 4,500 Da, or 5,000 Da. In some embodiments, the PEG may comprise linear chain molecules. In some embodiments, the chain may comprise branched molecules (e.g., 4-arm, 6-arm, or 8-arm star molecules). The fusion solution may be sterile. The fusion solution may be nonpyrogenic. In some embodiments, a 100 mL volume of the fusion solution may comprise approximately 100 mg PEG 3350 (e.g., USP PEG-3350). In some embodiments, the concentration of PEG may be between approximately 30% and 60%, between approximately 40% and 55%, or between approximately 45% and 50% (w/w). In some embodiments, the PEG is approximately 50% (w/w). The fusion solution may be made in ddi-$H_2O$ at a pH of approximately 7.4. In some embodiments, the pH may be between approximately 7.0 and 7.9.

A sealing solution (Solution 3) may comprise saline. The sealing solution may be isotonic. The sealing solution may comprise calcium. The sealing solution may be sterile. The sealing solution may be nonpyrogenic. In some embodiments, a 100 mL volume of the sealing solution may comprise approximately: 600 mg sodium chloride, USP (NaCl); 310 mg sodium lactate, USP ($C_3H_5NaO_3$); 30 mg potassium chloride, USP (KCl); and 20 mg calcium chloride, USP ($CaCl_2.2H_2O$). The sealing solution may be made in ddi-$H_2O$ at a pH of approximately 5.0. In some embodiments, the pH may be between approximately 4.0 and 6.5. In some embodiments, the sealing solution may be or may comprise lactated Ringer's solution.

PEG-Fusion Protocol

The method of using the kit and/or the solutions, described elsewhere herein, may comprise the sequential delivery of the pharmaceutical agents in solution. In preferred embodiments, the delivery of the therapeutic PEG-fusion solutions may be combined with neurorrhaphy, to repair a severed nerve. The method may comprise a multi-step process as described herein. In various embodiments, one or more steps may be removed where not essential to the outcome or altered. In various embodiments, one or more steps may be added to the method.

Contemporary surgical repair of severed peripheral nerves is conducted as an open surgical procedure consisting of rejoining the proximal and distal ends of the severed nerve with microsutures (neurorrhaphy). The treatment devices disclosed elsewhere herein can be configured to be used in conjunction with neurorrhaphy in the surgical repair of severed peripheral nerves.

In a first step, the surgical field for nerve repair may be prepared. The mechanism of nerve injury may be important. The treatment device and/or protocol may be configured to treat a narrow zone or indication of injury. In most cases, a neurolysis procedure may be used to allow for near tension-free repair. Neurolysis may temporarily degenerated the nerve fibers and/or relieve patient pain. In some implementations, a clean cut nerve stump can be desirable. The preparation may comprise trimming as necessary. A calcium-free hypotonic saline may be used for irrigation.

In a second step, the ends of the severed axons may be irrigated. The ends may be irrigated in a priming solution (Solution 1) as described elsewhere herein. The priming solution may comprise 1% methylene blue in hypotonic $Ca^{2+}$-free saline. In some implementations, the ends may be irrigated for approximately 1-2 minutes. The irrigation may advantageously increase axoplasmic volume, open cut axonal ends, expel intracellular membrane-bound vesicles, and/or prevent formation of new intracellular vesicles. These various effects of the priming solution may prepare the severed ends of the axons for cellular fusion, such as by promoting axon-to-axon contact in an optimal configuration of the cellular membranes for the agglutination and/or fusion of cells.

In a third step, the severed nerve may be physically rejoined resulting in an anastomosis. The rejoining may be performed with an operating microscope. The rejoining may comprise suturing the proximal and distal ends of the nerve together ("neurorrhaphy," the standard of care in clinical repair of severed nerves). The rejoining may be performed in the presence of a priming solution. The priming solution may be the same as that used in the second step (Solution 1). The rejoining may establish axon-to-axon contact within the epineurial sheath. In some instances, fusion may not occur if axons are not in direct contact across the repair site. The nerve may be sutured, in some embodiments, using a 8-0 nylon suture or another appropriate suture.

In a fourth step, the treatment device may be placed (e.g., gently positioned) such that the sutured nerve rests within the containment chamber of the device, as described elsewhere herein. In various embodiments, the anastomosis 52 of the nerve may be positioned approximately centrally within the containment chamber of the treatment device and/or in a deepest portion of the containment chamber configured to maximize exposure of the anastomosis to the applied solutions. The delivery device can provide a fluid containment field for isolated administration of and efficient removal of the fusion solution. In some embodiments, the rejoined nerve may be rinsed in a priming solution after being positioned within the treatment device, in addition to or alternatively to the earlier priming steps. The priming solution may be the same solution from the second step (Solution 1).

In a fifth step, fusion of the closely apposed axonal membranes of the severed axons may be induced. The fusion may be induced by exposure to a fusion solution (Solution 2). In some embodiments, the fusion solution may comprise about 50% w/w PEG/distilled water. The exposure may be about 1-2 minutes. The fusion solution can cause removal of bound cellular water thereby inducing membrane fusion. In various embodiments, the PEG concentration may be decreased below 50% or increased above 50%. The exposure time may be increased as the PEG concentration is decreased or decreased as the PEG concentration is increased. In some implementations, the PEG solution may not comprise more than approximately 50% (w/w) to prevent or minimize any deleterious effects of the PEG on the treated neurons.

In a sixth step, the fusion solution may be removed. The fusion solution may be removed by aspiration from the delivery device containment chamber. The aspiration may be performed by pipette, vacuum, syringe, or any other suitable fluid removal technique.

In a seventh step, the delivery device may be removed (e.g., gently) from around the nerve.

In an eighth step, any remaining membrane discontinuity of the fused axonal membranes may be sealed. The discontinuity can be sealed by rinsing with an excess volume of sealing solution (Solution 3). The sealing solution may comprise isotonic $Ca^{2+}$-containing saline as described elsewhere herein. The sealing solution may be applied for about 1-2 minutes. The sealing solution can induce formation of vesicles that seal any remaining axonal membrane holes. In some embodiments, the sealing solution may be applied to the nerve prior to removing the treatment device from the nerve, in addition to or alternatively to applying the sealing solution after the treatment device has been removed.

In a ninth step, routine wound closure and incision care may be performed, as necessary.

In some implementations, the sequence of these steps may be result-effective. In some embodiments, one or more of the solution application steps may be repeated more than once (e.g., two times, three times, etc.). The solutions may be reapplied sequentially after a previous volume of solution is removed. In some embodiments, the nerve may be rinsed between steps and/or between repeat applications of a solution. The rinsing solution may be a saline solution, such as a hypotonic $Ca^{2+}$-free saline solution or any other suitable solution. In some embodiments, the procedure may be performed without use of a treatment device or may use a device other than the device described herein.

Animal studies in nerve-PEG fusion have demonstrated superior speed of recovery as well as superior return of function compared to traditional nerve repair techniques. The PEG-fusion protocol can include a well-specified bioengineered sequence of chemicals, which may not be easily obtainable off the shelf (e.g., PEG 3,350 kD). A kit of solutions (and in some embodiments the treatment device) can provide great convenience to a surgeon. In some embodiments, the kit may have a shelf-life of at least 1-2 years (e.g., shelf-life of the PEG-fusion solutions). In various embodiments, one or more the solutions may be stored in containers under vacuum or under an inert gas (e.g., nitrogen or argon) to prevent oxidation. The solutions may be contained in containers that protect the solutions from radiation. The kit may comprise instructions for use and/or recommended volumes. The kit may comprise enough reagents for multiple surgeries or may be configured for a single use operation. The kit may optionally comprise one or more surgical tools or other tools, such as tools configured for handling and/or manipulating a treatment device, as described elsewhere herein.

What is claimed is:

1. A nerve treatment device for forming a fluid containment field around at least at least a portion of an isolated segment of a nerve, the nerve treatment device comprising:
    an elongate body extending from a first endwall to a second endwall substantially opposite the first endwall, the elongate body comprising a top surface and having a longitudinal axis extending from the first endwall to the second endwall;
    a handle extending laterally from the elongate body; and
    a containment chamber formed within the elongate body and extending from the first endwall to the second endwall, the containment chamber comprising a void volume intersecting the top surface to form an access area, the access area being configured to receive the isolated segment of the nerve into the containment chamber and the containment chamber being configured to substantially retain a volume of fluid within the void volume around at least a portion of the isolated segment of the nerve;
    wherein the first endwall comprises a first aperture opening into the containment chamber and the second endwall comprises a second aperture opening into the containment chamber, the first and second apertures being configured to retain first and second ends of the isolated segment of the nerve, respectively, and to form fluid seals around the first and second ends of the isolated segment of the nerve, respectively,
    wherein the first aperture and the second aperture are horizontally disposed more towards a front end of the elongate body,
    wherein the first endwall comprises a first slit extending through or along the first endwall from the top surface to the first aperture and the second endwall comprises a second slit extending through or along the second endwall from the top surface to the second aperture, the first slit intersecting a front edge of the first aperture, the second slit intersecting a front edge of the second aperture, and
    wherein at least a portion of the first endwall is flexible and configured to be biased, or a front wall is configured to be biased, in a manner that increases a first width between opposing edges of the first slit so that the nerve may be received through the first slit into the first aperture and wherein at least a portion of the second endwall is flexible and configured to be biased, or the front wall is configured to be biased, in a manner that increases a second width between opposing edges of the second slit so that the nerve may be received through the second slit into the second aperture.

2. The nerve treatment device of claim 1, wherein the flexible portion of the first endwall comprises a first flange having a thickness which tapers in a distal direction of the first flange, a distal edge of the first flange being defined by the first slit.

3. The nerve treatment device of claim 2, wherein the flexible portion of the first endwall comprises a second flange having a thickness which tapers in a distal direction of the second flange, a distal edge of the second flange being defined by the first slit, such that the distal edges of the first and second flanges form opposing edges of the first slit.

4. The nerve treatment device of claim 1, wherein the containment chamber is configured to retain the volume of fluid such that the fluid entirely surrounds a circumference of the nerve along at least a portion of the isolated segment of the nerve.

5. The nerve treatment device of claim 1, wherein the width of the access area is greater than a width of the first aperture and greater than a width of the second aperture.

6. The nerve treatment device of claim 1, wherein the first and second apertures are circular.

7. The nerve treatment device of claim 1, wherein the first and second apertures comprise diameters in an unbiased configuration slightly smaller than a diameter of the nerve such that the first and second apertures are configured to form a compressive seal around the nerve when received within the first and second apertures.

8. The nerve treatment device of claim 1, wherein the first and second apertures are longitudinally aligned.

9. The nerve treatment device of claim 1, wherein a bottom surface of the elongate body is generally rounded.

10. The nerve treatment device of claim 1, wherein at least a portion of the bottom surface of the elongate body is flattened so that the device may rest stably on a flat surface.

11. The nerve treatment device of claim 1, wherein the first endwall comprises a profile shape corresponding to a portion of an obround.

12. The nerve treatment device of claim 1, wherein the elongate body and the endwalls are integrally fabricated from the same material.

13. The nerve treatment device of claim 1, wherein the elongate body comprises silicone.

14. The nerve treatment device of claim 13, wherein the silicone comprises medical grade polydimethylsiloxane (PDMS).

15. The nerve treatment device of claim 1, wherein the first slit divides an inner front surface of the containment chamber from an inner surface of the first endwall and the second slit divides the inner front surface of the containment chamber from an inner surface of the second endwall, such that a front wall of the elongate body formed between the first slit and the second slit is configured to be biased in a frontward direction in a manner that increases the first width and the second width.

16. The nerve treatment device of claim 1, wherein a front wall of the elongate body comprises an angled edge on the top surface sloping downward toward the containment chamber.

17. A nerve treatment device for forming a fluid containment field around at least at least a portion of an isolated segment of a nerve, the nerve treatment device comprising:
   an elongate body extending from a first endwall to a second endwall substantially opposite the first endwall, the elongate body comprising a top surface and having a longitudinal axis extending from the first endwall to the second endwall;
   a handle extending laterally from the elongate body; and
   a containment chamber formed within the elongate body and extending from the first endwall to the second endwall, the containment chamber comprising a void volume intersecting the top surface to form an access area, the access area being configured to receive the isolated segment of the nerve into the containment chamber and the containment chamber being configured to substantially retain a volume of fluid within the void volume around at least a portion of the isolated segment of the nerve;
   wherein the first endwall comprises a first aperture opening into the containment chamber and the second endwall comprises a second aperture opening into the containment chamber, the first and second apertures being configured to retain first and second ends of the isolated segment of the nerve, respectively, and to form fluid seals around the first and second ends of the isolated segment of the nerve, respectively,
   wherein the first aperture and the second aperture are horizontally disposed more towards a front end of the elongate body,
   wherein the first endwall comprises a first slit extending through or along the first endwall from the top surface to the first aperture and the second endwall comprises a second slit extending through or along the second endwall from the top surface to the second aperture,
   wherein the first slit divides an inner front surface of the containment chamber from an inner surface of the first endwall and the second slit divides the inner front surface of the containment chamber from an inner surface of the second endwall, such that a front wall of the elongate body formed between the first slit and the second slit is configured to be biased in a frontward direction in a manner that increases the first width and the second width, and
   wherein at least a portion of the first endwall is flexible and configured to be biased, or a front wall is configured to be biased, in a manner that increases a first width between opposing edges of the first slit so that the nerve may be received through the first slit into the first aperture and wherein at least a portion of the second endwall is flexible and configured to be biased, or the front wall is configured to be biased, in a manner that increases a second width between opposing edges of the second slit so that the nerve may be received through the second slit into the second aperture.

* * * * *